(12) United States Patent
Rydberg

(10) Patent No.: US 7,718,437 B2
(45) Date of Patent: May 18, 2010

(54) METHOD FOR ANALYZING N-TERMINAL PROTEIN ADDUCTS

(75) Inventor: Per Rydberg, Enebyberg (SE)

(73) Assignee: Adduct Analys AB, Enebyberg (SE)

( * ) Notice: Subject to any disclaimer, the term of this patent is extended or adjusted under 35 U.S.C. 154(b) by 716 days.

(21) Appl. No.: 10/593,449

(22) PCT Filed: Apr. 13, 2005

(86) PCT No.: PCT/SE2005/000528

§ 371 (c)(1),
(2), (4) Date: Sep. 19, 2006

(87) PCT Pub. No.: WO2005/101020

PCT Pub. Date: Oct. 27, 2005

(65) Prior Publication Data

US 2007/0190659 A1      Aug. 16, 2007

Related U.S. Application Data

(60) Provisional application No. 60/562,985, filed on Apr. 19, 2004, provisional application No. 60/575,088, filed on May 28, 2004.

(30) Foreign Application Priority Data

Sep. 3, 2004     (SE)     .................... 0402122-6

(51) Int. Cl.
*G01N 33/72* (2006.01)
*G01N 33/00* (2006.01)
*C07D 233/86* (2006.01)
*C07D 233/00* (2006.01)

(52) U.S. Cl. ........................................... 436/86

(58) Field of Classification Search ............... 436/86, 436/161, 174, 176, 177
See application file for complete search history.

(56) References Cited

OTHER PUBLICATIONS

Kautiainen et al., A liquid chromatography tandem mass spectromertic method for in vivo dose monitoring of diepoxybutane, a metabolite of butadiene, 2000, Rapid Communications in Mass Spectrometry, 14, 1848-1853.*
Rydberg P. et al., Adducts to N-terminal valines in hemoglobin from butadiene metabolites, 1996, Chemico-Bio Interactions, 101, 193-205.*
Torbia A et al., Development of an Amino Acid Sequence and D/L Configuration Determination Method of Peptide with a New Fluorescence Edman Reagent, 7-Methylthio-4-(2, 1, 3-benzoxadiazolyl) Isothiocyanate, 2000, Anal. Chem., 72, 732-739.*
Muramoto et al., "Gas-phase Microsequencing of Peptides and Proteins with a Fluorescent Edman-type Reagnet, Fluorescein Isothiocyanate," Biosci. Biotech. Biochem., vol. 58, No. 2, pp. 300-304 (1994).
Per Rydberg et al, "Applicability of a Modified Edman Procedure for Measurement of Protein Adducts: Mechanisms of Formation and Degradation of Phenylthiohydantoins"; Chem. Res. Toxicol, 2002, vol. 15, pp. 570-581.
Steven G. Carmella et al, "Ethylation and methylation of hemoglobin in smokers and non-smokers"; Carcinogenesis, 2002, vol. 23, No. 11. pp. 1903-1910.
STN International, File CAPLUS, CAPLUS accession No. 1971-420961, document No. 75: 20961, Kawauchi, Hiroshi; Tuzimura, Katura, "Reaction of fluorescein-isothiocyanate with proteins and amino acids III. Syntheses of trifluoroacetic acid salts of fluorescein-thiohydantoin amino acids and their spectrometric studies"; Agricultural and Biological Chemistry (1971), 35(2), 150-7.
Matsunaga et al., "Development of an Efficient Amino Acid Sequencing Method Using Fluorescent Edman Reagent 7-[(N,N-Dimethylamino)sulfonyl]-2-1,3-benzoxadiazol-4-7I Isothiocyanate", Anal. Chem., Dec. 1, 1995, vol. 67, No. 23,pp. 4276-4282.
Zoellner et al., "Flurometric and Mass Spectrometric Analysis of Nonenzymatic glycosylated Albumin", Biochemical and Biophysical Research Communications, 2001, vol. 284, No. 1, pp. 83-89.
Ding et al., "Reactivity of tolmetin glucuronide with human serum albumin: identification of binding sites and mechanisms of reaction by tandem mass spectrometry", Drug Metabolism and Disposition, 1995, vol. 23.

* cited by examiner

*Primary Examiner*—Walter D Griffin
*Assistant Examiner*—Christine T Mui
(74) *Attorney, Agent, or Firm*—Young & Thompson

(57) ABSTRACT

Method for analyzing adducts in a fluid and/or a solid material suspected of containing the adducts by bringing the material in contact with an isothiocyanate reagent containing a fluorescent. The reagent do not have the isothiocyanate group directly bound to an unsubstituted phenyl or pentafluorophenyl group. A method for manufacturing a standard material for use in the analyzing method, a standard material obtainable by this manufacturing method. Compounds suitable for use as standard material and use of the standard material, and a container for analyzing the adducts are also disclosed. A method for analyzing hazardous substances, a kit including standard material or a compound set out above, an apparatus for performing the analyzing method, and a computer program stored on a data carrier for performing the analyzing method or the manufacturing method are also disclosed.

45 Claims, 19 Drawing Sheets

Figure 1. Principles of the N-alkyl Edman procedure[a].
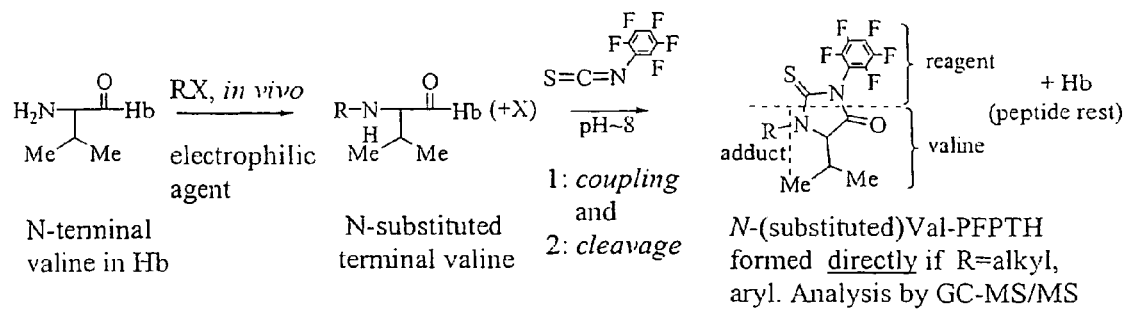
Footnote: [a]Phenyl isothiocyanate and pentafluorophenyl isothiocyanate have been utilized in this procedure.

Figure 2. Principles of the present method of the first aspect
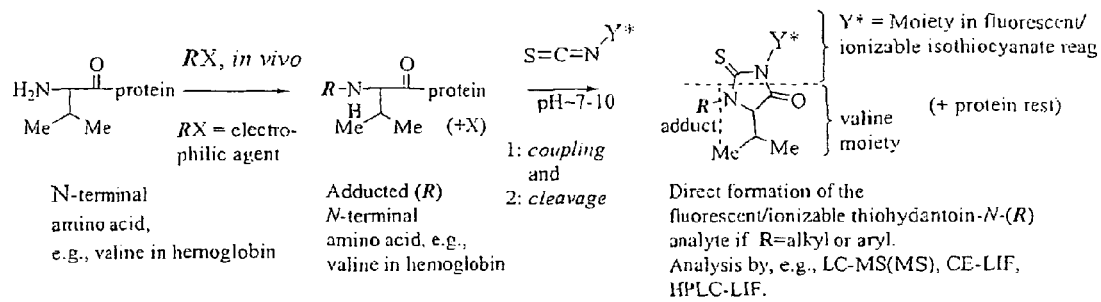

Figure 3. The reactions and reagents studied: coupling between selected isothiocyanate reagents (Y-N=C=S) and valine itself (R=H, X=O) or bound (R= alkyls) to a peptide (X=LeuSer) or protein (X=rest of human globin).
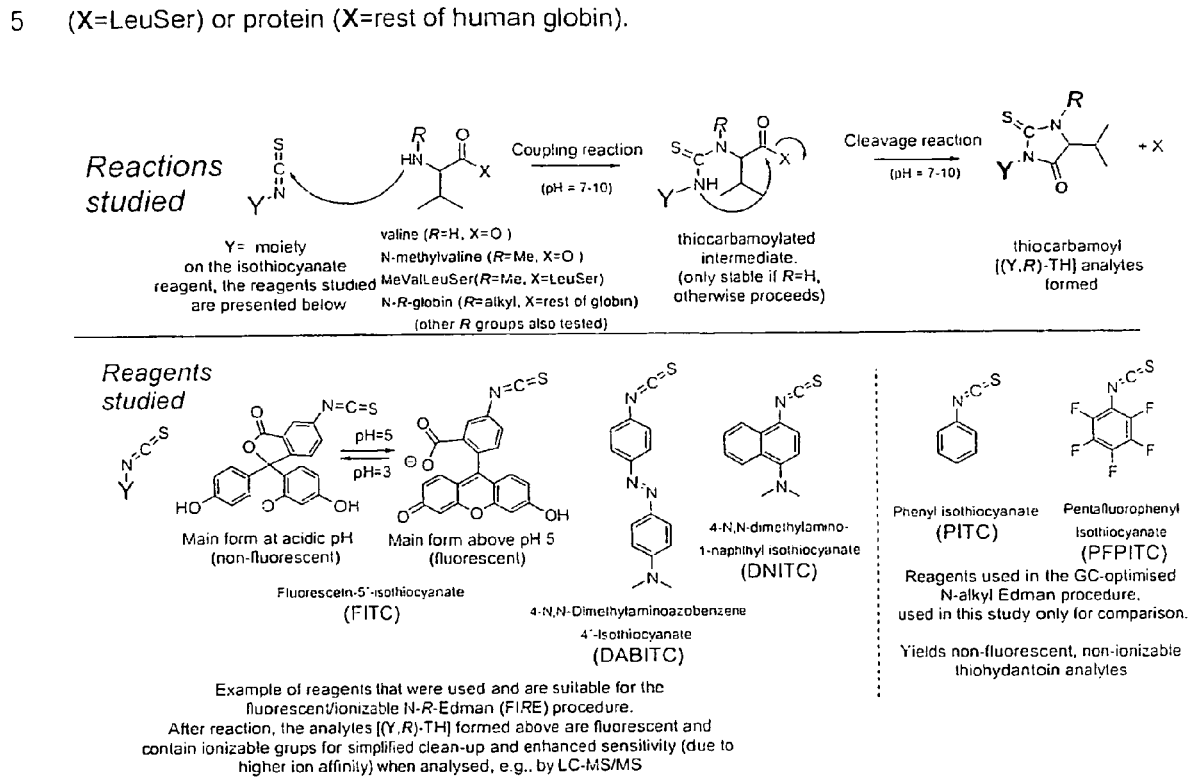

Figure 4. General structure of the adducted analytes and proposed adducted analytes formed in the present method from N-terminal valine, e.g., in proteins such as globin (XTH-$R$-Val)[a] and of analytes formed from N-terminal asparagine, e.g., in proteins such as bovine serum albumin (XTH-R-Asp-$R_2$)[b].

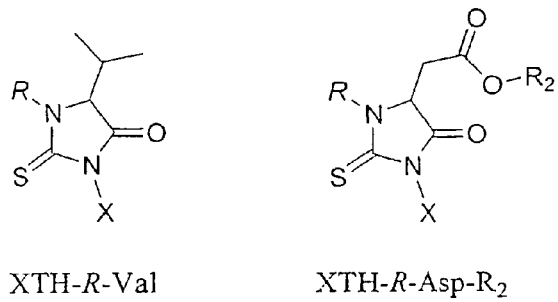

XTH-$R$-Val        XTH-$R$-Asp-$R_2$

Footnotes: [a]The $R$ substituent in the valine thiohydantoin represents any adduct (e.g., alkyl and aryl or substituted homologues of alkyl and aryl, but not hydrogen) covalently bound to the valine nitrogen. The X substituent in the valine thiohydantoin represents the moiety of any isothiocyanate reagent utilized in which the isothiocyanate group is directly bound to an aromatic ring or an aromatic ring system, thereby providing fluorescent and/or ionizable and/or other valuable properties to the analyte. However, X is not a phenyl, 4-bromophenyl, 4-methoxyphenyl or pentafluorophenyl group, e.g., PITC and PFPITC.

The $R$ substituent in the asparagine thiohydantoin represents any adduct (e.g., alkyl and aryl or substituted homologues of alkyl and aryl, but not hydrogen) covalently bound to the valine nitrogen. The X substituent in the asparagine thiohydantoin represents the moiety of any isothiocyanate reagent utilized in which the isothiocyanate group is directly bound to an aromatic ring or an aromatic ring system, thereby providing fluorescent and/or ionizable and/or other valuable properties to the analyte. However, X is not a phenyl, 4-bromophenyl, 4-methoxyphenyl or pentafluorophenyl group, e.g., PITC and PFPITC. The $R_2$ substituent on the carboxyl group of asparagine represents hydrogen; an alkyl, aryl, carboxyl or benzyl group; or substituted analogues of these. This carboxyl group can also be an anion.

Figure 5. Studied thiohydantoin analytes.

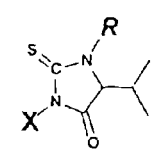

| Analyte | (nr) | Adduct (R) | Reagent used (X) |
|---|---|---|---|
| PTH-Val | 1 | R=H | PITC |
| PTH-MeVal | 2 | R=Me | PITC |
| PFPTH-MeVal | 3 | R=Me | PFPITC |
| PFPTH-HOEtVal | 4 | R=CH$_2$CH$_2$OH | PFPITC |
| DABTH-Val | 5 | R=H | DABITC |
| DABTH-MeVal | 6 | R=Me | DABITC |
| DNTH-Val | 7 | R=H | DNITC |
| DNTH-MeVal | 8 | R=Me | DNITC |
| FTH-Val | 9 | R=H | FITC |
| FTH-MeVal | 10 | R=Me | FITC |
| FTH-AAVal | 11 | R= CH$_2$CH$_2$CONH$_2$ | FITC |
| FTH-GAVal | 12 | R=CH$_2$CH(OH)CONH$_2$ | FITC |
| FTH-HOC$_{18}$Val | 13 | R=CH$_2$CH(OH)(CH$_2$)$_{15}$CH$_3$ | FITC |
| FTH-HOPrVal | 14 | R=CH$_2$CH(OH)CH$_2$ | FITC |
| FTH-CholEOVal (adduct from cholesterol-5α,6α-epoxide) | 15 | R=C$_{27}$H$_{47}$O | FITC |
| FTH-GlcVal (adduct formed after reduction of glycosylated N-terminal) valine in peptide and globin | 16 | R=CH$_2$[CH(OH)]$_4$CH$_2$OH | FITC |

Figure 6. Separation of FTH-Val (9) and FTH-MeVal (10) by capillary electrophoresis employing detection with a diode array. FTH-Val (9) elutes after 7.44 min and FTH MeVal (10) elutes after 8.91 min (17 mM phosphate buffer, pH 7, containing 20 mM SDS). Conditions 30 kV, 52 cm capillary, 1 nL sample injected.
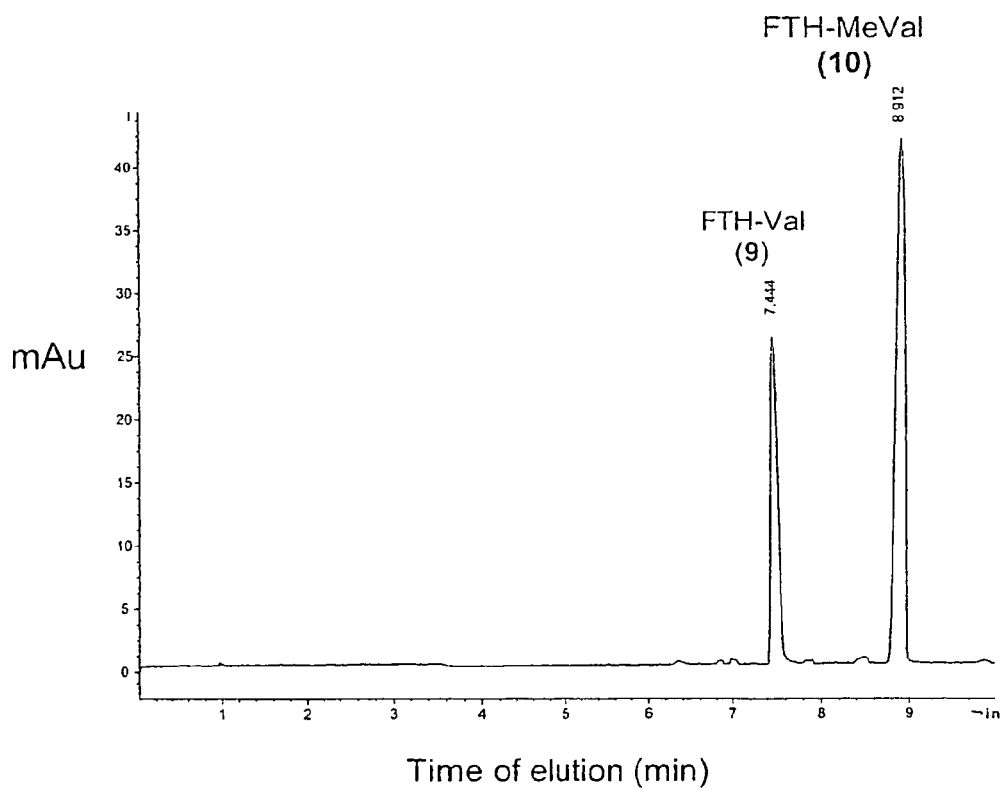

Figure 7. Fluorescence measurements[a]: the excitation and emission spectra of FTH-Val (9) at various concentrations.

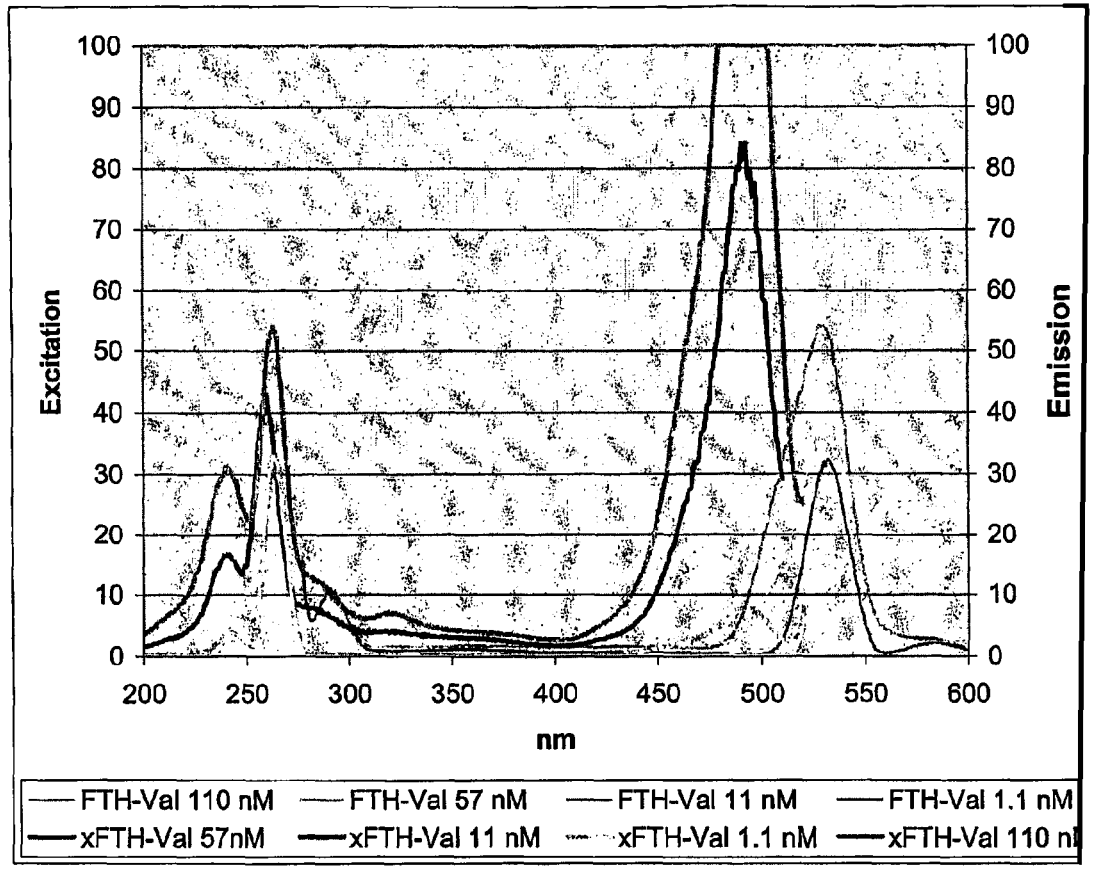

Footnote: [a] FTH-Val (9) dissolved in acetonitrile:aqueous buffer (1:9), pH 7, at different concentrations. Excitation wavelength 265nm, emission scan 275-600nm; and emission wavelength 517 nm, excitation scan 200-510nm. The bold lines (xFTH-Val) represent the excitation spectra, while the thin lines (FTH-Val) depict the emission spectra.

Figure 8. Fluorescence measurements[a]: the excitation and emission spectra of 1.1 μM FTH-MeVal (10) at pH 1, 4, 7 and 9.

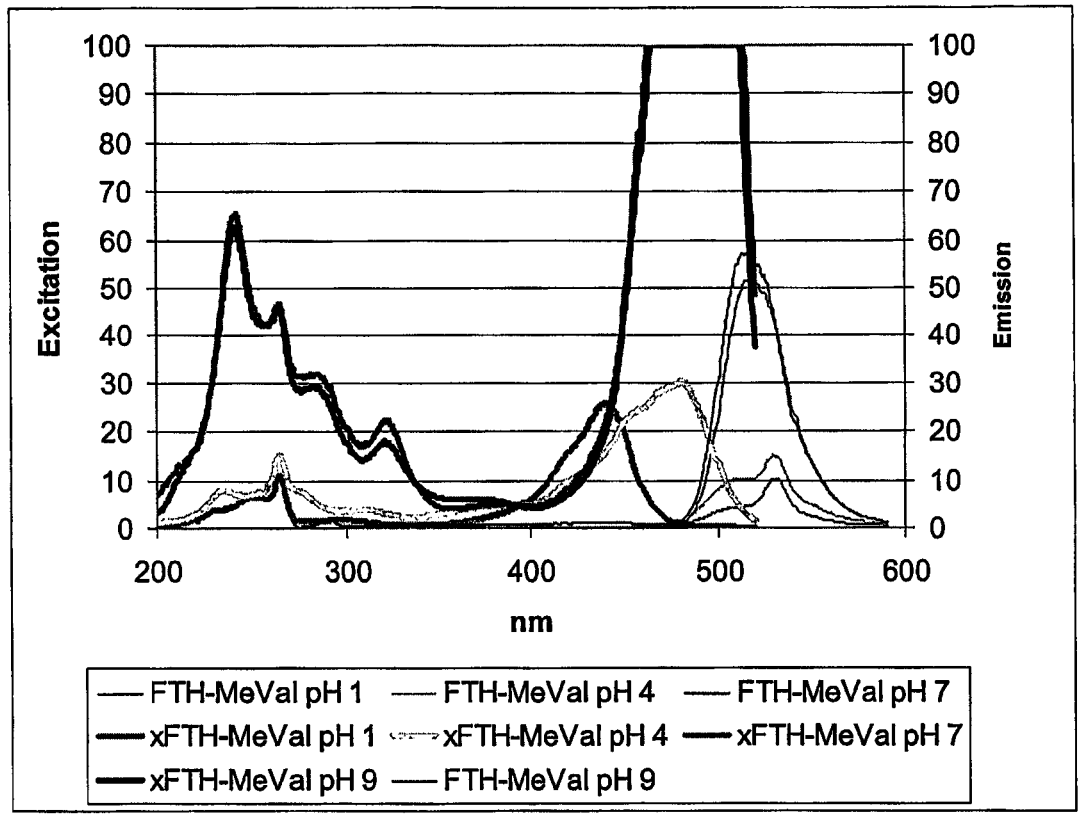

Footnote: [a]The analytes were dissolved in acetonitrile:aqueous buffer (1:9). Slits 5/5; excitation wavelength 265 nm, emission scan 275-600 nm; and emission wavelength at 530 nm, excitation scan 200-520 nm. The bold lines (xFTH-MeVal at pH 1, 4, 7 and 9) represent the excitation spectra, while the thin lines (FTH-MeVal pH 1, 4, 7 and 9) depict the emission spectra.

Figure 9. Fluorescence measurements[a]: the excitation and emission spectra of 2.5 µM DABTH-MeVal at pH 1, 4, 7 and 9.

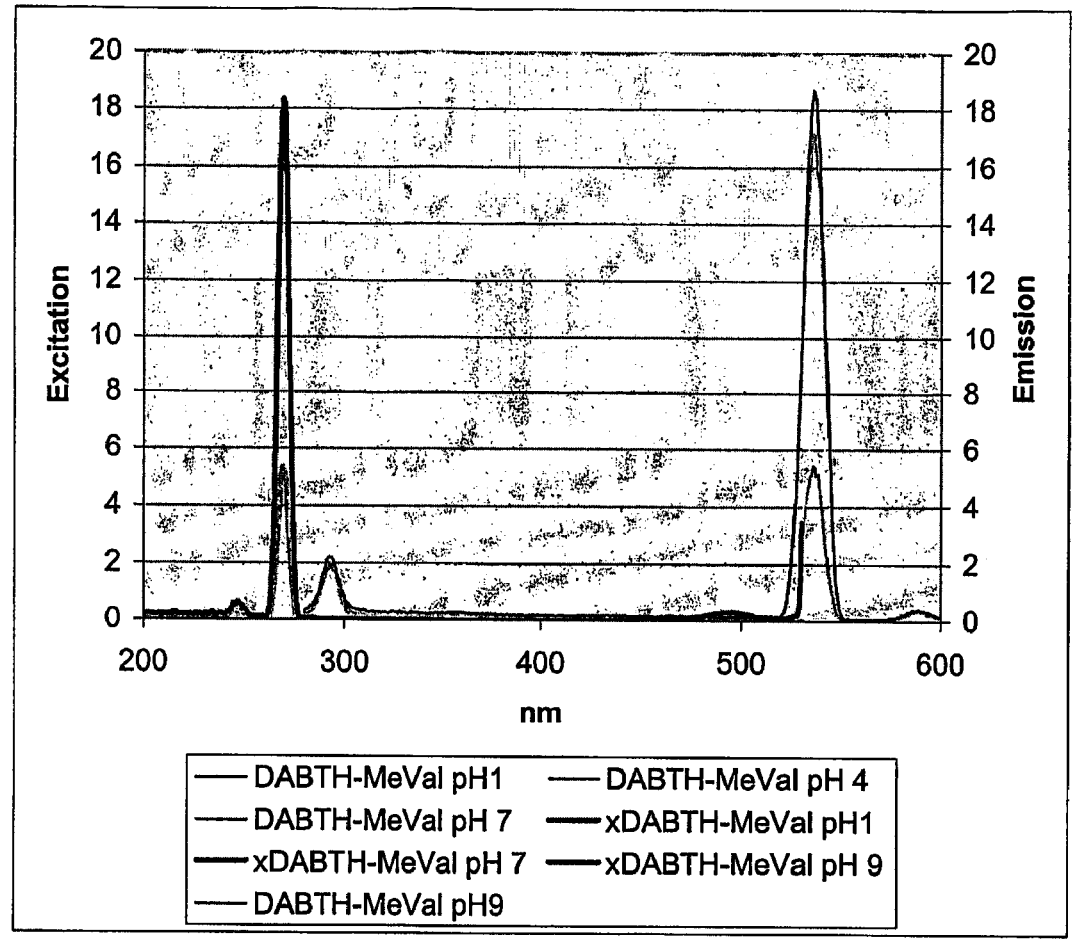

Footnote: [a]The analytes dissolved in acetonitrile:aqueous buffer (1:9). Slits 5/5; excitation wavelength 268 nm, emission scan 280-600 nm; and emission wavelength 538 nm, excitation scan 200-530 nm. The bold lines (xDABTH-MeVal) represent the excitation spectra, while the thin lines (DABTH-MeVal pH) depict the emission spectra.

Figure 10. Comparative studies[a] of the excitation and fluorescence emission spectra for the analytes DABTH-MeVal (6), DNTH-Val (7), FTH-MeVal (10), using fluoranthene as a reference.

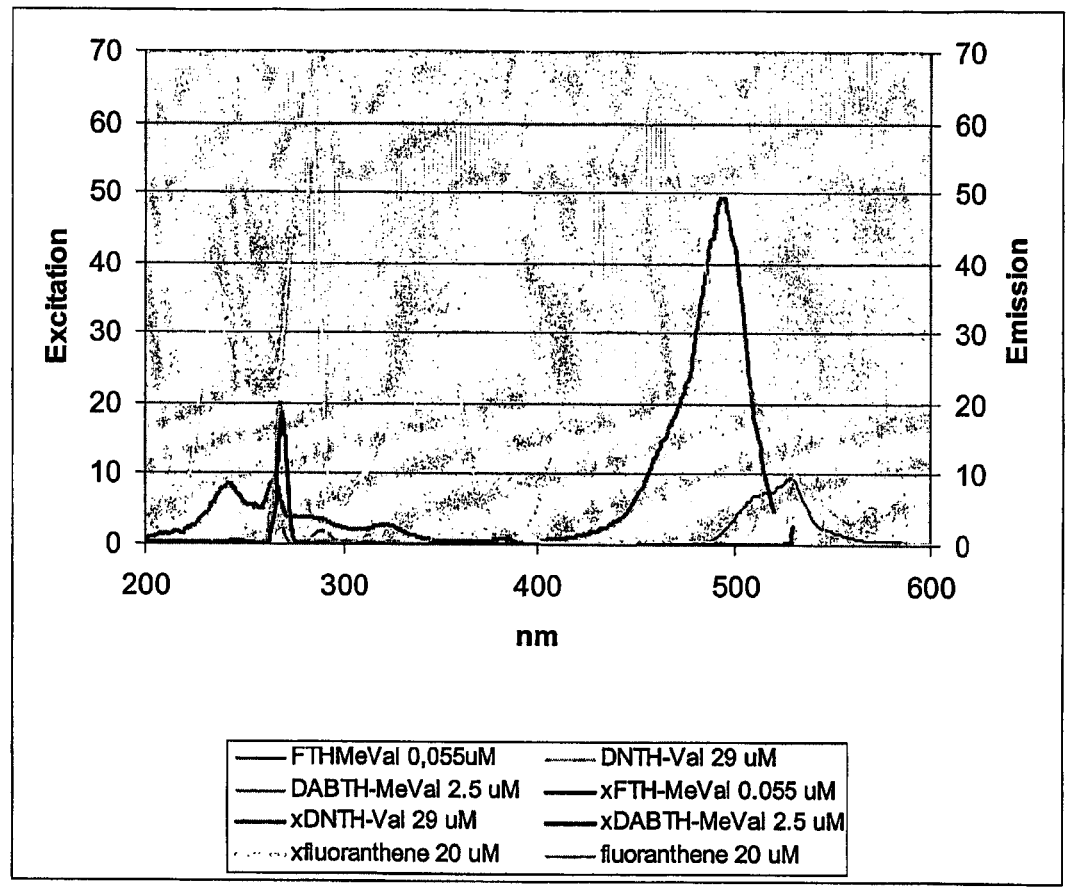

Footnote: [a]The compounds were dissolved in acetonitrile:aqueous buffer (1:9) at a pH suitable for each analyte. Slits 5/5 and locked excitation/emission wavelength suitable for each analyte. The bold lines represent the excitation spectra, while the thin lines depict the emission spectra.

Figure 11. Fluorescence measurements[a]: the excitation and emission spectra of 1.5 µM DNTH-MeVal at pH 1, 4, 7 and 9.

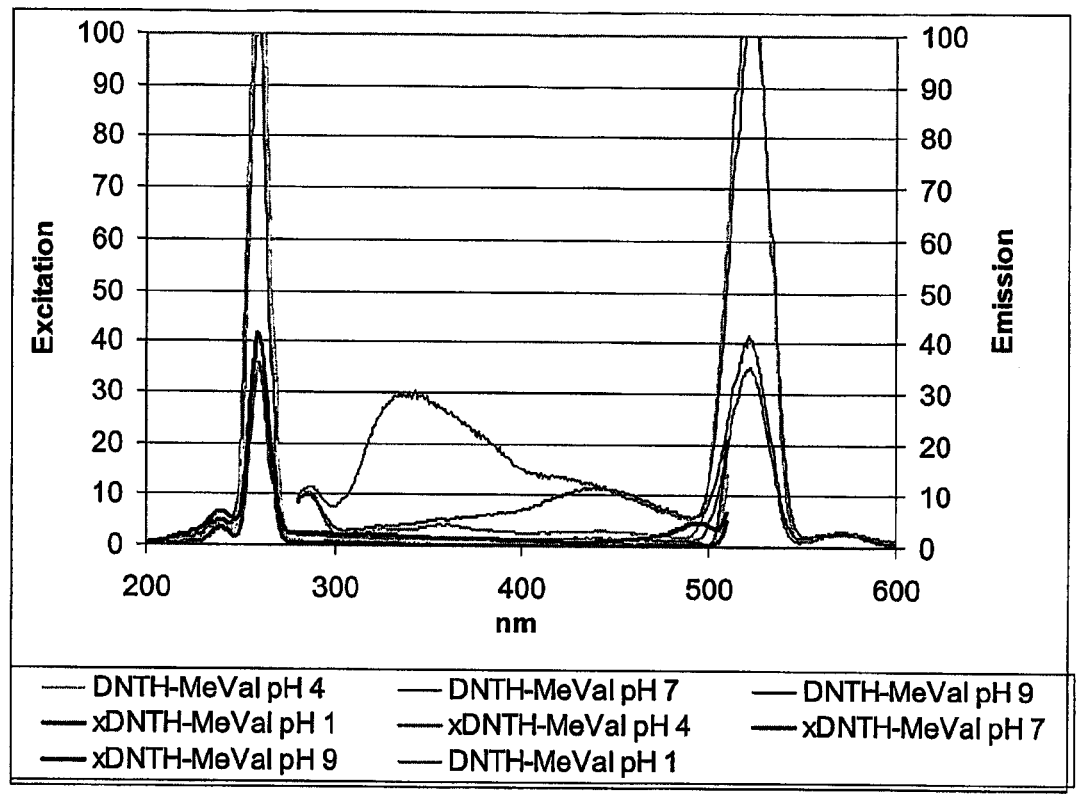

Footnote: [a]The compounds were dissolved in acetonitrile:aqueous buffer (1:9). Slits 10/10; excitation wavelength 260 nm; emission scan 270-600 nm and emission wavelength 520 nm, excitation scan 200-510 nm. The bold lines (xDNTH-MeVal) represent the excitation spectra, while the thin lines (DNTH-MeVal) depict the emission spectra.

Figure 12. UV absorbance of selected analytes in acetonitrile, using fluoranthene as reference.
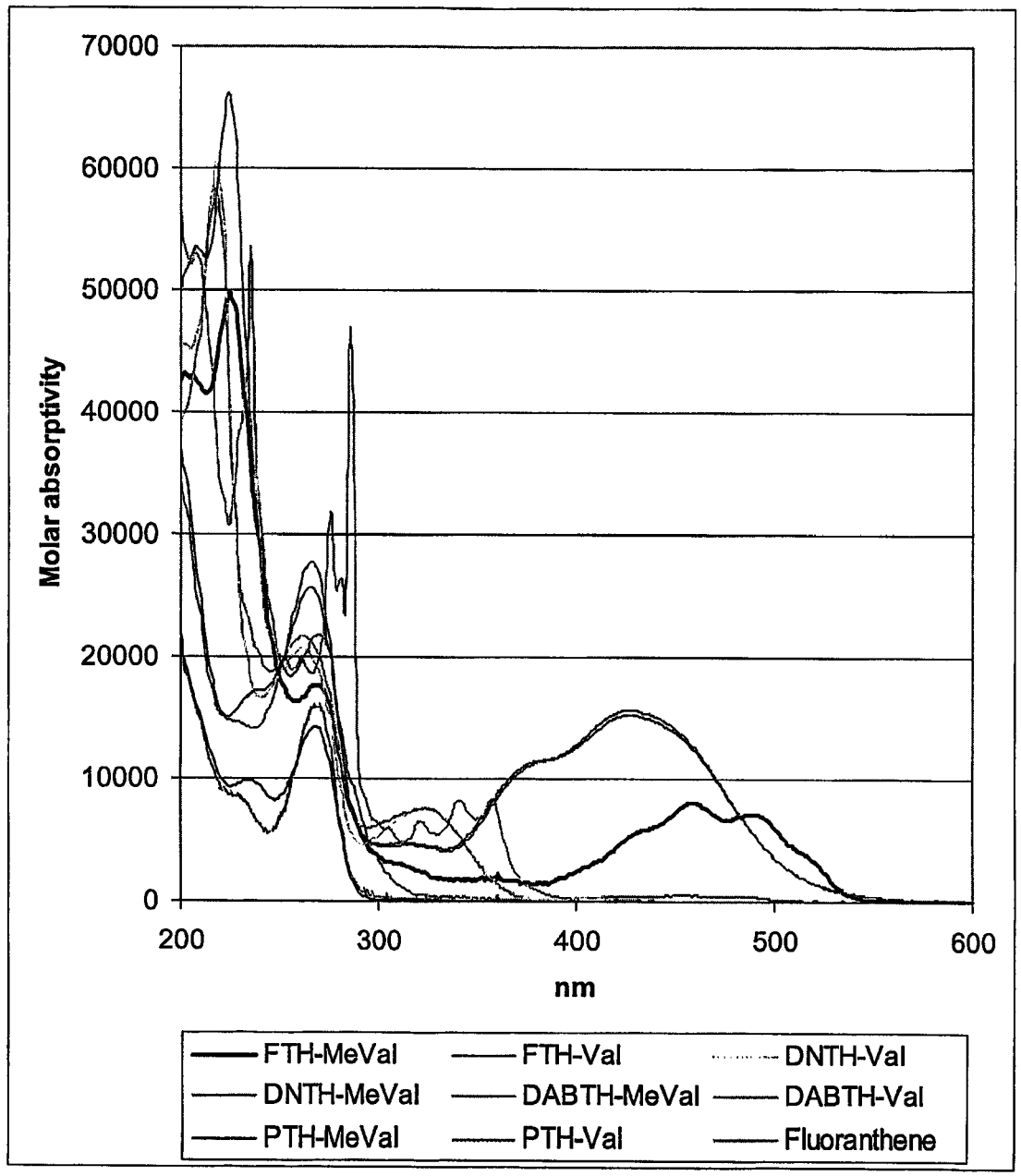

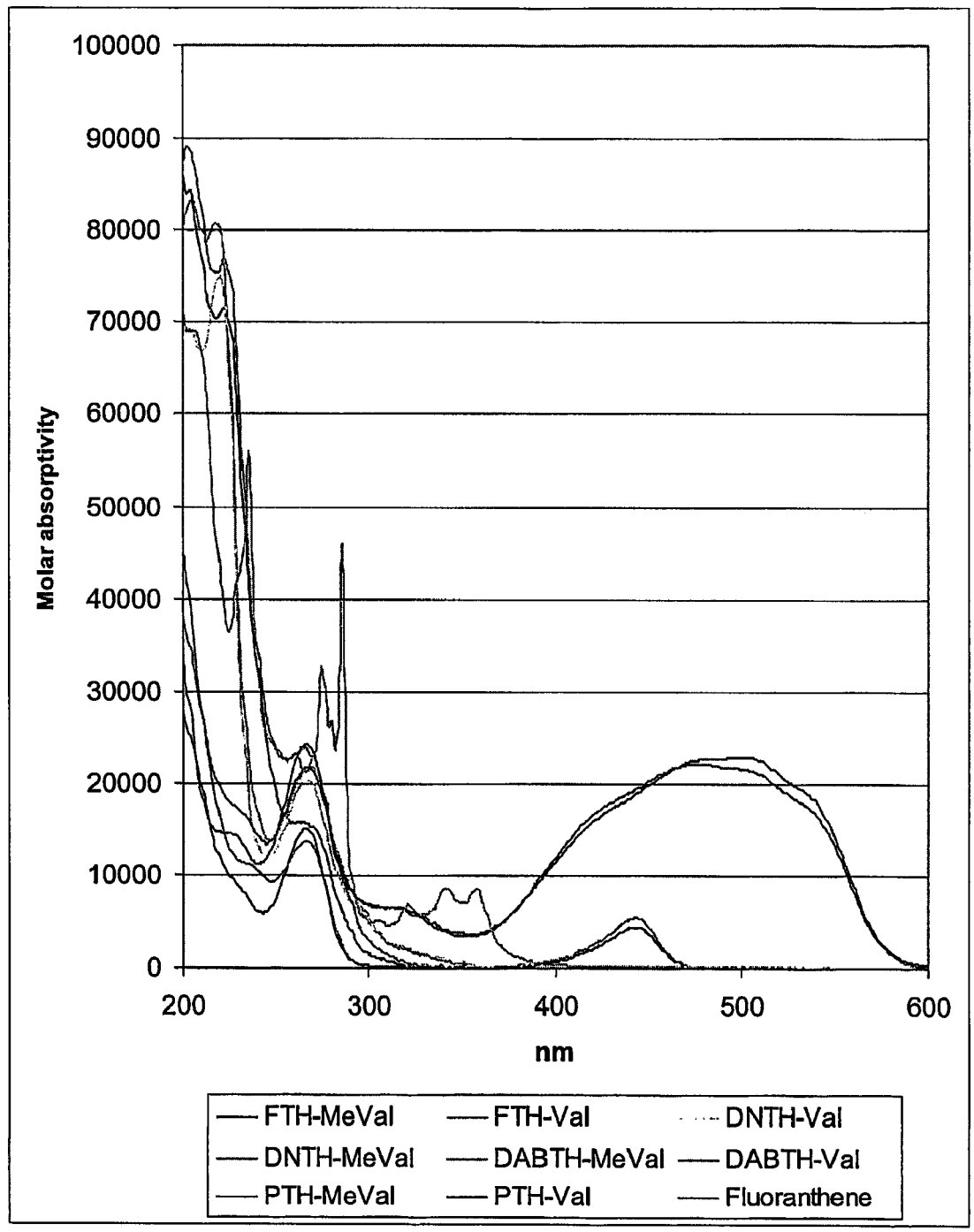
Figure 13. UV absorbance for selected analytes dissolved in acetonitrile/water (1/1) containing 0.1 % TFA, using fluoranthene as reference.

Figure 14. LC-MS/MS analysis of acrylamide adducts of human globin using the present method, in comparison with reference compounds.
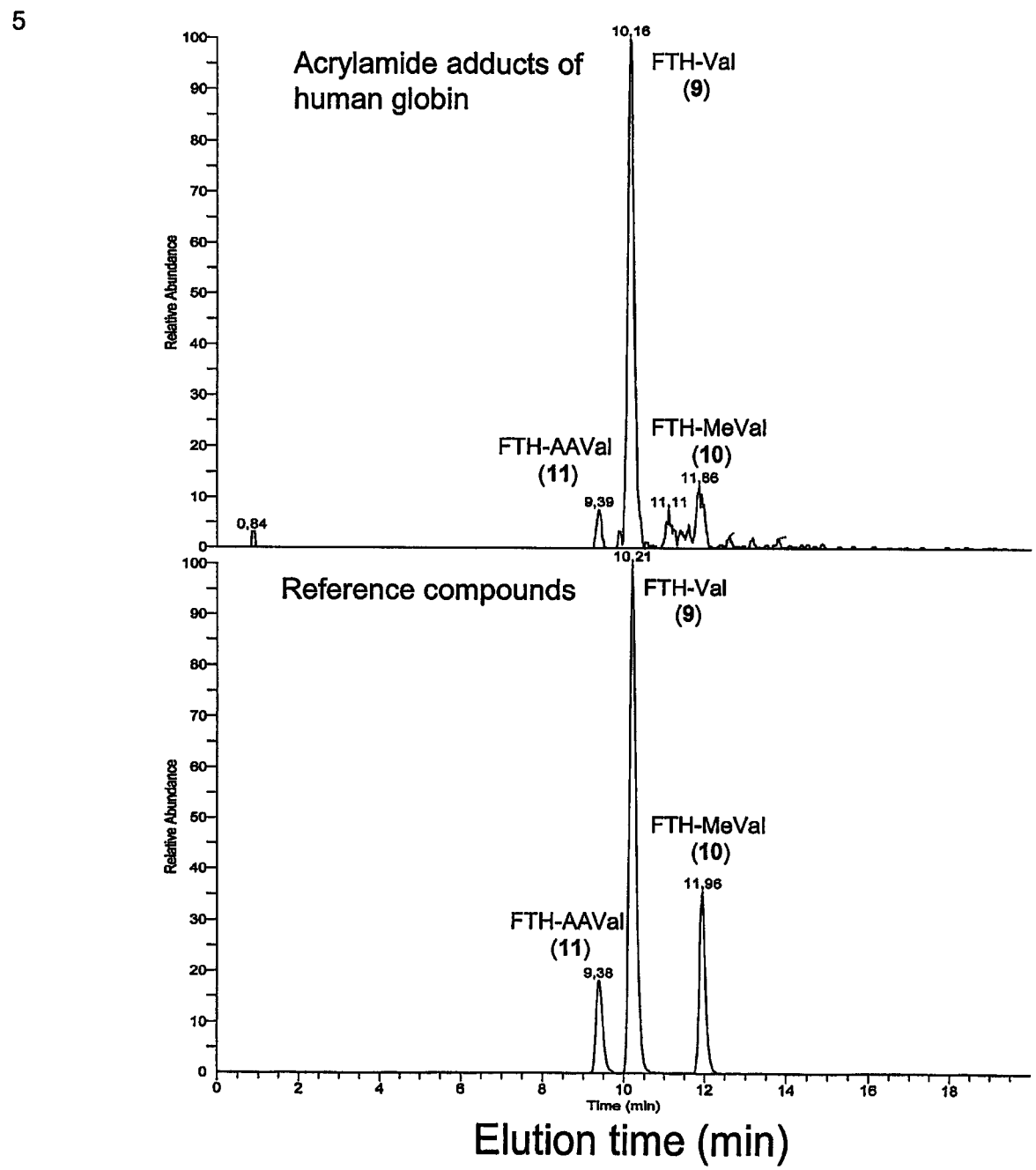

Figure 15. Fluorescence measurements[a]; the excitation and emission spectra of 0.1μM FTH-Val (9) and FTH-MeVal (10) at pH 7.

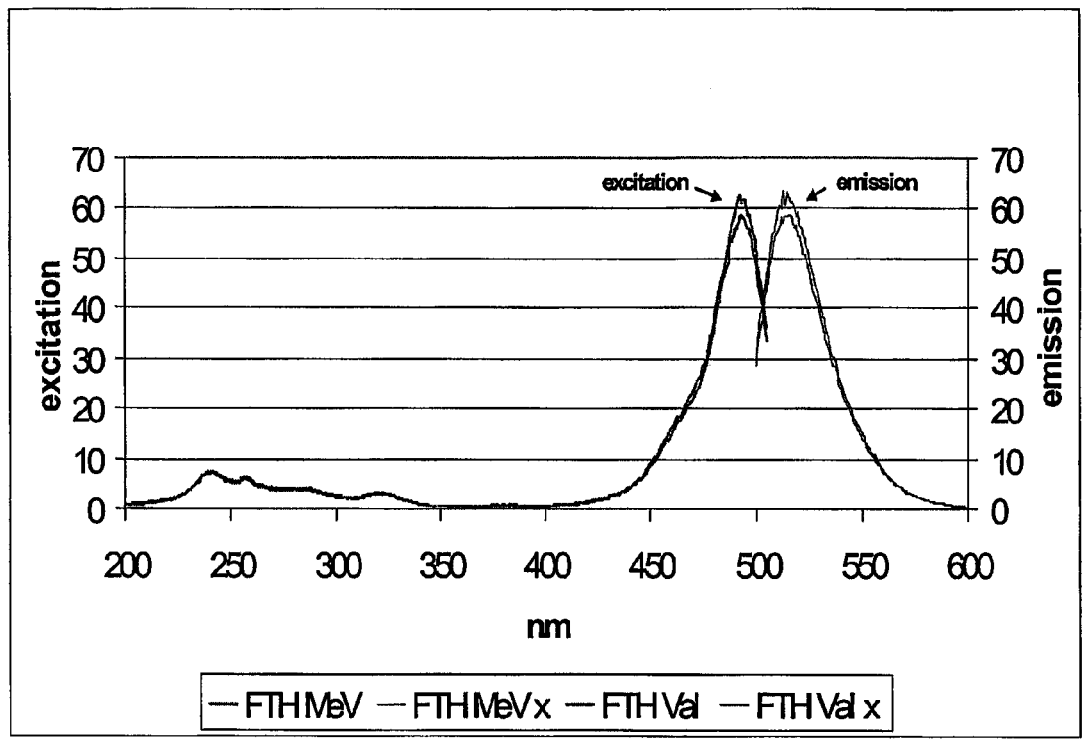

Footnote: [a]The analytes were dissolved in acetonitrile:aqueous buffer (1:9). Slits 5/5; excitation wavelength 492 nm, emission scan 500-600 nm; and emission wavelength 515 nm, excitation scan 200-505 nm. The bold lines represent the excitation spectra; while the thin lines (x) depict the emission spectra.

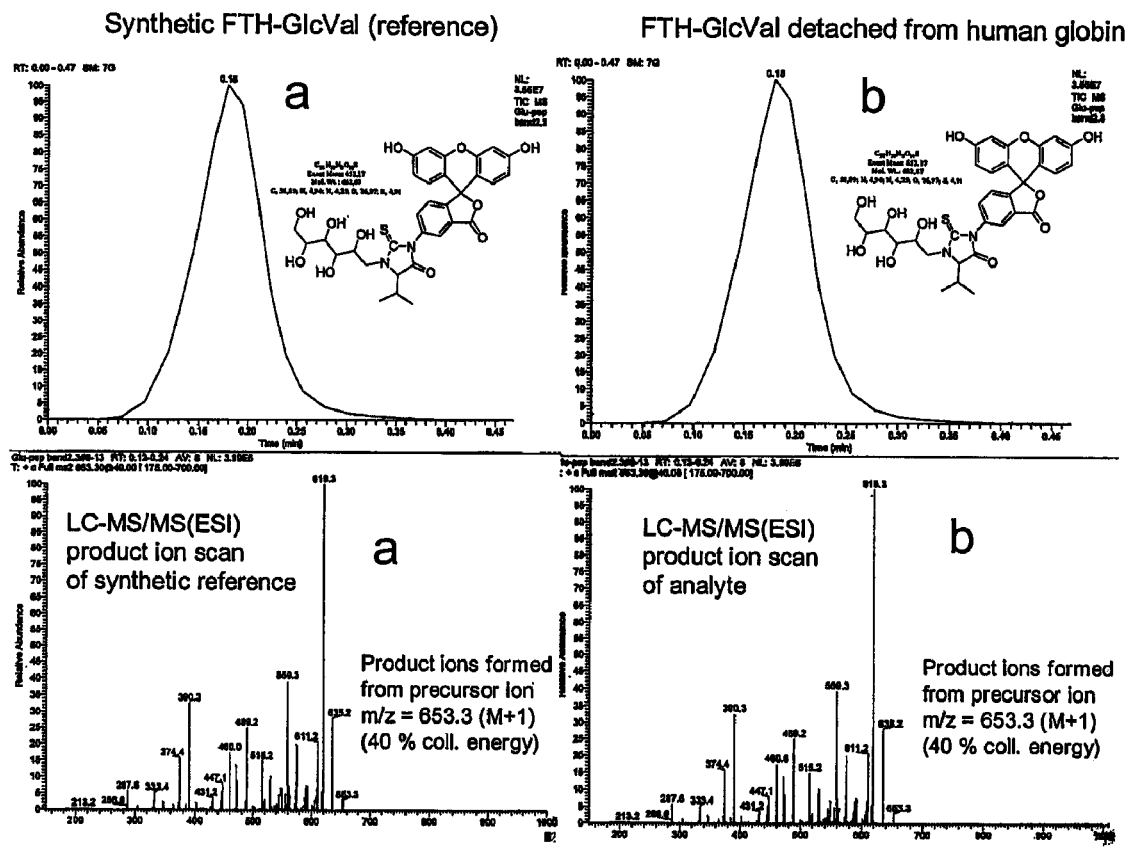
Figure 16. LC-MS/MS analysis of: FTH-GlcVal (a) formed from a glycosylated, reduced model dipeptide and of FTH-GlcVal (b) formed from glycosylated reduced globin.

Figure 17. Comparison of the relative sensitivities (presented on a log scale) obtained by determination of the limits of detection (LOD) of LC-MS/MS in the ESI and APCI modes.
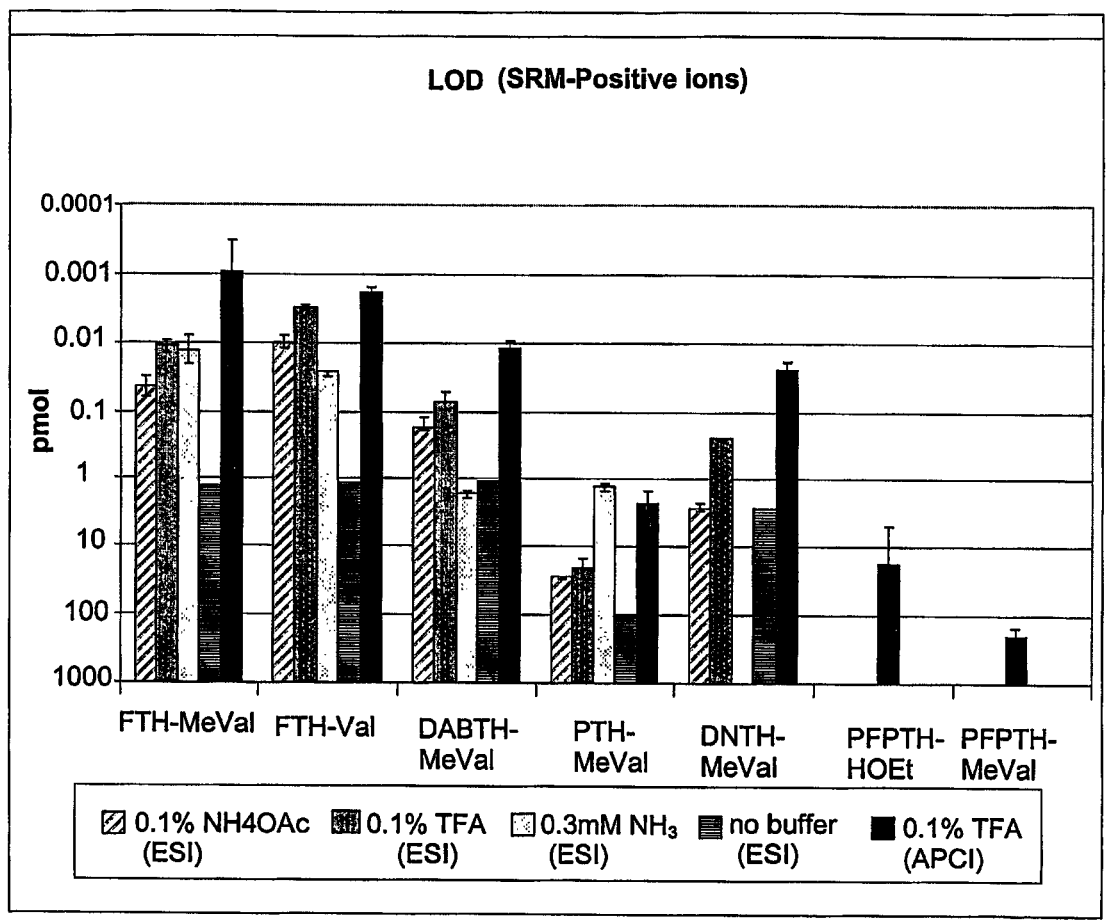

Figure 18. Comparison of the relative sensitivities (presented on a log scale) obtained by determinations of the limits of detection (LOD) of LC-MS/MS in the ESI and APCI modes.
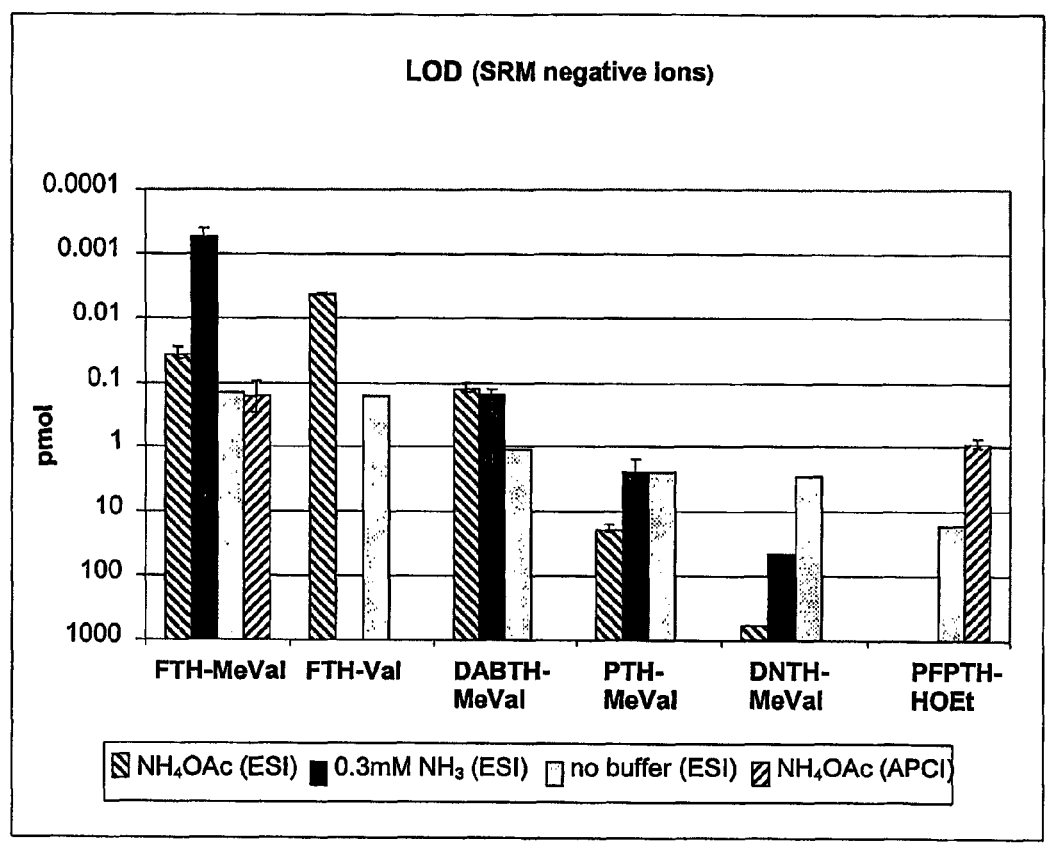

Figure 19. Illustration of a simplified approach to sample preparation and clean-up based on the principles of the fluorescent/ionizable N-R-Edman procedure.
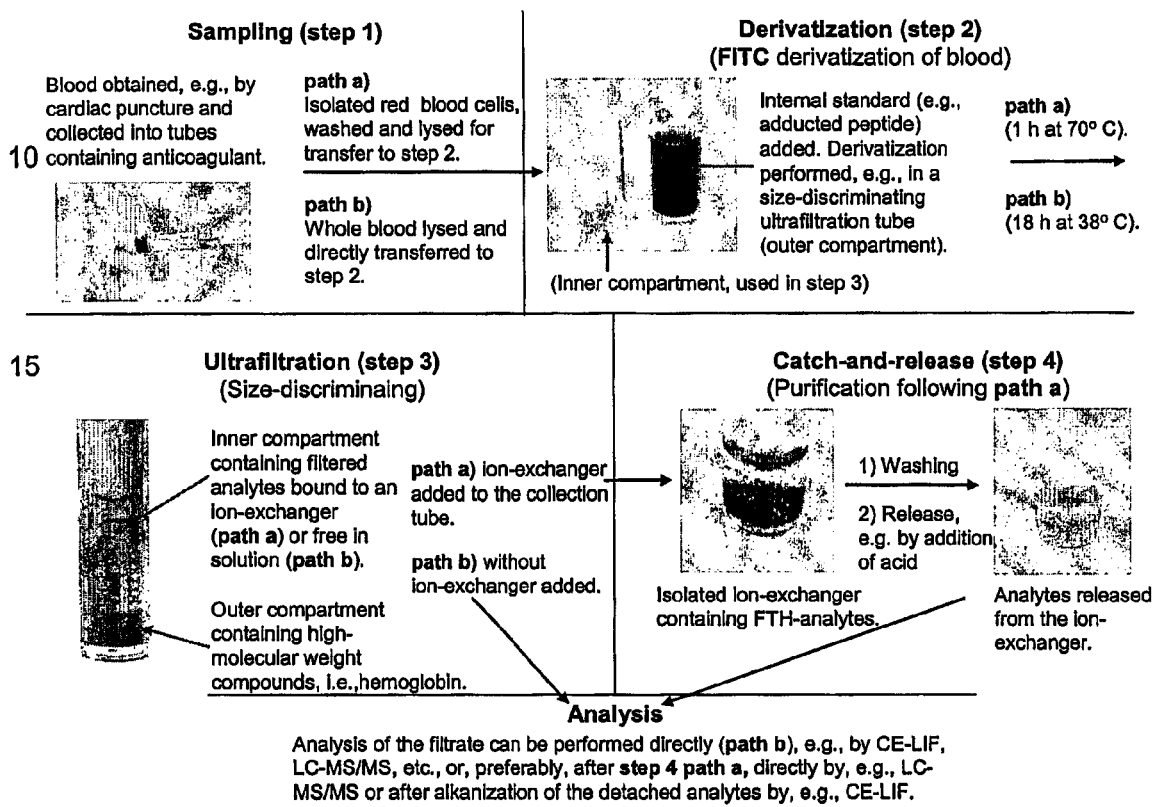

METHOD FOR ANALYZING N-TERMINAL PROTEIN ADDUCTS

This invention concerns the technical field of analyzing adducts. In particular the present invention relates to a fluorescent/ionizable N-R-Edman procedure for analysis of N-terminal protein adducts using spectrophotometric and/or mass spectrometric detection. Further, the invention relates to products required for the above-mentioned method and uses of said products and said method.

BACKGROUND

It has been demonstrated earlier that electrophilic compounds present in vivo can be monitored by measuring the products (adducts) of their reaction with proteins, in particular hemoglobin (Hb) (1-5). Important nucleophilic sites in proteins, e.g., hemoglobin (Hb), which are reactive under physiological conditions are the imidazole nitrogen atoms in histidine residues, sulfur atoms in cysteine and methionine residues, oxygen atoms in carboxyl groups and in hydroxyl groups in tyrosine and serine residues, and the α-nitrogen atoms in the N-terminal valine residue of all four chains of human Hb (6).

The so-called N-alkyl Edman procedure was developed for measurements of adducts (mainly low-molecular weight adducts) to N-terminal valine residues in Hb (7). This method was based on the original Edman degradation procedure (8,9) used for protein sequencing. It was observed that N-terminal valine N-alkylated with a radioactively labeled 2-hydroxyethyl moiety from ethylene oxide was released spontaneously as a phenylthiohydantoin (PTH) under the conditions (pH>7) employed for the coupling reaction between phenyl isothiocyanate (PITC) and protein. The released PTH could be separated from unmodified N-terminal valine residues, as well as from the rest of the protein by means of extraction.

This observation led to the development of the N-alkyl Edman procedure for gas chromatographic (GC)/mass spectrometric (MS) determination of Hb adducts (10). Because of its usefulness, the N-alkyl Edman method has been applied in a number of laboratories for research purposes, dose monitoring and hygienic surveillance (11-16).

A brief description of the N-alkyl Edman procedure is presented in FIG. 1. A sample of the globin (isolated from red blood cells by acid precipitation) is dissolved in formamide. Pentafluorophenyl isothiocyanate (PFPITC) is then added, together with a small amount of aqueous 1 M NaOH in order to obtain a near-neutral solution. This mixture is maintained at room temperature overnight, after which the temperature is raised to 45° C. for approximately two hours (17). The pentafluorophenylthiohydantoin (PFPTH) derivatives of the terminal N-alkylvaline residues are released in high yield by this procedure and can subsequently be isolated by extraction (liquid-liquid).

Although the N-alkyl Edman procedure has become an established method for analysis of N-substituted hemoglobin adducts, the method has its restrictions, e.g., the range of adducts that can be analyzed is limited. Small adducts, e.g., involving ethylene oxide and propylene oxide, can be quantified at the pmol/g globin level, which is sensitive enough for measurement of background adduct levels (levels without known exposure). However, adducts with a few polar groups are more difficult to analyse, due to the limitations imposed by the GC separation system prior to MS detection. Some of these limitations can be solved, e.g., by further derivatisation of the polar groups (18). However, this approach is both time-consuming and demands the development of new procedures for each specific adduct. Furthermore, adducts of high molecular weight (>500 mass units, mu) and/or thermolabile adducts are extremely difficult to analyze using the GC-MS based N-alkyl Edman procedure.

Accordingly, there is a need for more versatile and sensitive, as well as simpler methods for analyzing adducts.

SUMMARY OF THE INVENTION

One or more of the above problems are solved by the present invention which provides according to a first aspect a method for analyzing adducts in a fluid and/or a solid material suspected of containing said adducts comprising the following steps:

a) bringing said fluid and/or solid material in direct contact with an isothiocyanate reagent containing a fluorescent and, preferably, also an ionizable moiety, with the exception of a reagent in which the isothiocyanate group is directly bound to an unsubstituted phenyl or pentafluorophenyl group [i.e., the reagent contains an —N=C=S (isothiocyanate) group, preferably directly bound to an aromatic ring or aromatic ring system, but where said group is not bound to an unsubstituted phenyl, 4-bromophenyl, 4-methoxyphenyl or pentafluorophenyl group (i.e., PITC or PFPITC)];

b) allowing said reagent to react with adducted N-terminals in proteins or peptides present in said fluid and/or solid material;

c) separating the analytes formed from the reaction mixture; and d) detecting the analytes formed, and optionally visualizing the result.

This first aspect of the invention, i.e., the fluorescent/ionizable N-R-Edman procedure, overcomes one or more of the problems set out above and provides improved sensitivity and increases the range of applicability. The invention is based on the principles of the original N-alkyl Edman procedure; adducted N-terminals can be detached with high selectivity in comparison to unmodified (normal) N-terminals and measured as their corresponding thiohydantoin derivatives after coupling with isothiocyanate Edman reagents.

According to a second aspect of the present invention it also provides a method for manufacturing a standard material for use in the first aspect of the present invention comprising the following steps:

i) reacting an adducted N-terminal in a protein or a peptide with a reagent containing a fluorescent and/or ionizable moiety, with the exception of a reagent in which the isothiocyanate group is directly bounded to an unsubstituted phenyl or pentafluorophenyl group; and ii) purifying the analyte formed (standard material in this case), which is preferably a thiohydantoin analyte formed, by, e.g., separating the unreacted compound from the reaction mixture.

According to a third aspect of the present invention it also provides a standard material obtainable by the second aspect of the present invention. In a fourth aspect, the present invention also provides a compound selected from among the group of 3-[4-(4-dimethylamino-phenylazo)-phenyl]-5-isopropyl-1-methyl-2-thioxo-imidazolidin-4-one (DABTH-MeVal); 3-(4-dimethylamino-naphthalen-1-yl)-5-isopropyl-1-methyl-2-thioxo-imidazolidin-4-one (DNTH-MeVal); fluorescein, 5-(4-isopropyl-3-methyl-2-thioxo-imidazolidin-5-one) (FTH-MeVal); fluorescein, 5-[4-isopropyl-3-(2-carbamoyl-ethyl)-2-thioxo-imidazolidin-5-one] (FTH-AAVal);

fluorescein, 5-[4-isopropyl-3-(2-carbamoyl-2-hydroxyethyl)-2-thioxo-imidazolidin-5-one] (FTH-GAVal); fluorescein, 5-[4-isopropyl-3-(2-hydroxyoctadecyl)-2-thioxo-imidazolidin-5-one] (FTH-HOC$_{18}$Val); fluorescein, 5-[4-isopropyl-3-(2-hydroxy-propyl)-2-thioxo-imidazolidin-5-one] (FTH-HOPrVal); fluorescein, 5-{4-isopropyl-3-[17-(1,5-dimethyl-hexyl)-3,5 and/or 6-dihydroxy-10,13-dimethyl-hexadecahydro-cyclopenta[a]phenanthren-5 and/or 6-yl])-2-thioxo-imidazolidin-5-one} (FTH-CholEOVal) and fluorescein, 5-[4-isopropyl-3-(2,3,4,5,6-pentahydroxy-hexyl)-2-thioxo-imidazolidin-5-one] (FTH-GlcVal).

A fifth aspect of the present invention is that it also provides for the use of a standard material according to the third aspect or a compound according to the fifth aspect, which also is a standard material, in connection with the method according to the first aspect. The method according to the first aspect is preferably run initially with a standard material according to the third aspect or with a compound according to the fifth aspect, whereby values which may be used in a standard curve, are obtained. Thereafter the method of the first aspect is performed whereby values are obtained (which can be plotted in a curve) from which the presence of the analyte can be quantitated by comparing the standard curve (or the corresponding values) with the curve obtained when running a sample (or its corresponding values).

A sixth aspect of the present invention is that it also provides a container for use when analyzing adducts in a fluid or a solid material suspected of containing said adducted compounds, in which said container steps a)-c) set out in the first aspect above can be performed. The present invention also provides in a seventh aspect, a method according to the first aspect for analyzing hazardous substances, such as acrylamide, ethylene oxide, and epoxides formed in vivo, e.g., glycidamide from acrylamide, styrene oxide from styrene and aflatoxin B1 epoxide from aflatoxin B1. An eight aspect of the present invention is that it also provides a kit comprising standard material according to the third aspect or a compound according to the fourth aspect. According to a ninth aspect the present invention provides an apparatus for performing the method according to the first aspect providing means for performing steps a)-c) as set out above and for the detection in step d) as set out above. According to a tenth aspect the present invention provides a computer program stored on a data carrier for performing the method according to the first aspect or the method according to the second aspect.

Accordingly, hereby a novel method is introduced for the analysis of electrophilic compounds measured in vivo as their corresponding adducts by means of a fluorescent/ionizable N-R-Edman procedure. The principle of this procedure is presented in FIG. 2. This invention is based on the original observation that N-alkylated N-terminal protein adducts are detached with high selectivity from adducted proteins as their corresponding N-alkyl-valine phenylthiohydantoines after derivatisation with phenyl isothiocyanate (PITC) or pentafluorophenyl isothiocyanate (PFPITC) in the so called N-alkyl Edman procedure. In the present procedure, according to the first aspect of the present invention, fluorescent and, also, preferably, ionizable Edman reagents are used (e.g., the isothiocyanates; FITC, DNITC and DABITC), which after reaction with adducted N-terminals in proteins are detached and analyzed as their corresponding thiohydantoines. In contrast to the N-alkyl Edman method, the present method according to the first aspect of the invention is designed to yield analytes which have physical and chemical properties suitable for isolation, separation and analysis in liquid-based systems.

DETAILED DESCRIPTION OF THE INVENTION

It is intended throughout the present description that the expression "analyte" includes any analyte formed after bringing a fluid and/or solid material in direct contact with an isothiocyanate reagent containing a fluorescent and, preferably, also an ionizable moiety, with the exception of a reagent in which the isothiocyanate group is directly bound to an unsubstituted phenyl or pentafluorophenyl group.

It is intended throughout the present description that the expression "adducted N-terminal" includes any type of covalently alkylated, arylated or by other means modified N-terminal protein or peptide, but in particular N-terminals in hemoglobin, serum albumin and myoglobin, preferably an N-terminal valin.

It is intended throughout the present description that the expression "LC" includes any type of liquid chromatography, but in particular HPLC, i.e., High-Performance Liquid Chromatography.

It is intended throughout the present description that the expression "MS" includes any type of mass-spectrometry, e.g., MS or MS/MS.

It is intended throughout the present description that the expression "CE" includes any type of capillary electrophoresis.

It is intended throughout the present description that the expression "LIF" includes any type of laser induced fluorescence detection. Preferably, LIF is used in connection with LC, thus achieving LC-LIF.

According to a preferred embodiment of the first aspect of the invention, the detection step d) is followed by a step e) involving comparison of the results from this detection step d) with previously obtained results, obtained using steps a)-d), which previously obtained results emanate from a standard material formed from the adduct under scrutiny, and, optionally, calculating a quotient between said results and, optionally, presenting said quotient visually.

According to a preferred embodiment of the first aspect of the invention formation of said adduct has involved three secondary N-terminals; valine in Hb, asparagine in serum albumin and glycine in myoglobin.

According to a preferred embodiment of the first aspect of the invention, said adduct is a globin adduct.

According to a preferred embodiment of the first aspect of the invention, said adduct is a hemoglobin or a myoglobin adduct.

According to a preferred embodiment of the first aspect of the invention, said adduct is a serum albumin adduct.

According to a preferred embodiment of the first aspect of the invention, said reagent is a fluorescent compound or a compound that forms fluorescent thiohydantoin analytes.

According to a preferred embodiment of the first aspect of the invention, said reagent is an ionizable compound that forms ionizable thiohydantoin analytes.

According to a preferred embodiment of the first aspect of the invention, said reagent is a fluorescein compound or a derivative thereof.

According to a preferred embodiment of the first aspect of the invention, said reagent is an isothiocyanate reagent containing a fluorescent moiety and an ionizable moiety, preferably selected from the group consisting of 4-isothiocyanato-benzoic acid, 4-isothiocyanato-naphthalene-1-carboxylic acid, 10-isothiocyanato-anthracene-9-carboxylic acid, (4-isothiocyanato-phenyl)-dimethyl-amine, 9-Isothiocyanato-acridine, 4-isothiocyanato-quinoline, malachite green isothiocyanate, FITC, DNITC and DABITC or a derivative thereof; most preferably FITC, DNITC and DABITC or a derivative thereof; and especially most preferably FITC. The FITC may be 5' or 6' (isomer I and II).

According to a preferred embodiment of the first aspect of the invention, step c) is performed using LC and/or CE and step d) using LIF and/or fluorescence detection. The detection in step d) is performed by illuminating the reaction product (analyte) present and then measuring the emitted energy or the absorbed energy using LIF or diode array, preferably LIF.

According to a preferred embodiment of the first aspect of the invention, step c) is performed using CE and/or LC and step d) using UV detection; preferably, step c) is performed using CE and step d) using a diode array UV detector (DAD). After LC or capillary electrophoresis, the reaction product (analyte) present is illuminated and the emitted energy or the absorbed energy is measured.

According to a preferred embodiment of the first aspect of the invention, step c) is performed using LC and step d) using MS detection.

According to a preferred embodiment of the first aspect of the invention, step c) is performed using gel electrophoresis and step d) using fluorescence detection.

According to a preferred embodiment of the first aspect of the invention, step c) is performed using CE and said CE step is followed by transferring the analyte present onto a rotary device, preferably a disc, after which step d) is performed using fluorescence detection which involves illuminating the analyte present and measuring the emitted energy or the absorbed energy, whereby illumination of the analyte present and measurement the emitted energy or the absorbed energy thereof may be performed an unlimited number of times.

According to a preferred embodiment of the first aspect of the invention, step c) is preceded by a step for enriching the analyte present. Said enrichment step preceding step c) is preferably performed using protein precipitation or size-discriminating ultrafiltration, preferably followed by an ion-exchanging step or ultracentrifugation, preferably followed by an ion-exchanging step. Instead of ultracentrifugation or size-discriminating ultrafiltration it would be plausible to use osmotic principles, conventional liquid-liquid extraction, protein precipitation (e.g., with ethanol or acetonitrile) or to use solid phase extraction (SPE) techniques to separate the un-reacted from the reacted compounds. When FITC or a derivative thereof is used in said method, an anion exchanger is preferably used in the ion-exchanging step, and when DNITC or DABITC or a derivative thereof is used, a cation exchanger is preferably used in the ion-exchanging step.

According to a preferred embodiment of the first aspect of the invention, said analyte is a compound according to formula I or II or a derivative thereof,

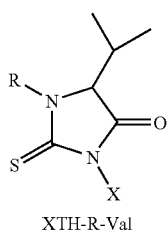

XTH-R-Val

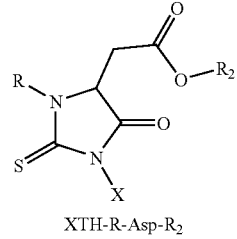

XTH-R-Asp-R$_2$ wherein R represents any adduct (e.g., alkyl and aryl or substituted analogues thereof, with the exception of hydrogen) and X represents a moiety of any isothiocyanate reagent utilized in which the isothiocyanate group is directly bound to an aromatic ring or an aromatic ring system, thereby providing fluorescent and/or ionizable properties to the analyte, with the exception that X is not a phenyl, 4-bromophenyl, 4-methoxyphenyl or pentafluorophenyl group, and R$_2$ represents hydrogen, alkyl, aryl, carboxyl, benzyl or substituted analogues thereof, or a carboxyl anion group.

According to a preferred embodiment of the first aspect of the invention, detection of the analyte in step d) is performed at a pH above 5, preferably at a pH of about 7.

According to a preferred embodiment of the first aspect of the invention, the illumination wavelength in step d) is, e.g., for FITC analytes 488 nm (±20 nm) and the measurement of the emitted energy is performed at longer wavelengths, e.g., 515 nm.

According to a preferred embodiment of the first aspect of the invention said fluid and/or solid material is blood or processed blood, preferably of human origin, which has been obtained at an earlier stage, preferably contained in a container, most preferred a tube.

According to a preferred embodiment of the first aspect of the invention step a) is preceded by obtaining blood from a subject, preferably by cardiac puncture, and collecting said blood in a container, preferably a tube containing anti-coagulant, whereupon the blood is processed; and wherein step b) is followed by heating. The blood may obviously also be blood already obtained as set out earlier above.

According to a preferred embodiment of the first aspect of the invention said blood is processed either by centrifugation, washing and lysating, or lysating only. The lysating may preferably be done either by freezing (at approximately −20° C.) or directly by ultrasonication (during approximately 10 minutes).

According to a preferred embodiment of the first aspect of the invention said centrifugation, washing and lysating is followed by heating at approximately 70° C., preferably during approximately 1 h.

According to a preferred embodiment of the first aspect of the invention said lysating only, is followed by heating at approximately 38° C., preferably during approximately 18 h.

According to a preferred embodiment of the first aspect of the invention step b) is performed in a size-discriminating ultra filtration tube, preferably in the outer tube of said ultra filtration tube.

According to a preferred embodiment of the first aspect of the invention the heating is followed by step c) as set out in claim 1 wherein the separation is performed by size-discriminating ultra filtration in a size-discriminating ultra filtration tube and whereupon the analyte is being bound to an ion exchange resin in said tube and thereupon purifying said analyte.

According to a preferred embodiment of the first aspect of the invention the purifying of said analyte is performed by first washing the resin to which the analyte is bound and release the analyte from the resin, preferably by adding an acid (most preferred TFA), to said resin, and subsequently filter the resin off giving the analyte in the remaining filtrate.

According to a preferred embodiment of the first aspect of the invention the detecting as set out in step d) of the first aspect of the invention is performed by using CE-LIF or LC-MS/MS, preferably LC-MS/MS. Alkalization is preferably performed of the detached analytes is before detecting using CE-LIF.

According to a preferred embodiment of the first aspect of the invention said heating is followed by step c) as set out in the first aspect of the invention wherein the separation is performed by size-discriminating ultra filtration in a size-discriminating ultra filtration tube and wherein the analyte is free in solution and present in the filtrate.

According to a preferred embodiment of the first aspect of the invention the detecting as set out in step d) of the first aspect is performed by using CE-LIF or LC-MS/MS.

Preferably, a standard material according to the second aspect of the invention is subjected first to the above method according to the first aspect of the invention, whereby i), ii) or a combination of both is used, which allows a first scan that can show where the adduct of interest would appear if present in the sample. Using this standard material first, will provide information concerning where the analyte, the adducted thiohydantoin derivative, appears and how the analyte behaves during the detection step.

According to a preferred embodiment of the second aspect of the invention said adduct is an N-adducted amino acid or adducted N-terminal peptide/protein.

According to a preferred embodiment of the second aspect of the invention, said adduct is a globin adduct.

According to a preferred embodiment of the second aspect of the invention, said adduct is a hemoglobin or a myoglobin adduct.

According to a preferred embodiment of the second aspect of the invention, said adduct is a serum albumin adduct.

According to a preferred embodiment of the second aspect of the invention, said reagent is a fluorescent compound or a compound that forms fluorescent thiohydantoin analytes.

According to a preferred embodiment of the second aspect of the invention, said reagent is an ionizable compound that forms ionizable thiohydantoin analytes.

According to a preferred embodiment of the second aspect of the invention, said reagent is a fluorescein compound or a derivative thereof.

According to a preferred embodiment of the second aspect of the invention, said reagent is an isothiocyanate reagent comprising a fluorescent moiety and a ionizable moiety, preferably selected from the group consisting of 4-isothiocyanato-benzoic acid, 4-isothiocyanato-naphthalene-1-carboxylic acid, 10-isothiocyanato-anthracene-9-carboxylic acid, (4-isothiocyanato-phenyl)-dimethyl-amine, 9-isothiocyanato-acridine, 4-isothiocyanato-quinoline, malachite green isothiocyanate, FITC, DNITC and DABITC or a derivative thereof; most preferably, FITC, DNITC and DABITC or a derivative thereof; and especially most preferably FITC. Further, the FITC may further be 5' or 6' (isomer I and II).

According to a preferred embodiment of the second aspect of the invention, said analyte is a compound according to formula I or II or a derivative thereof,

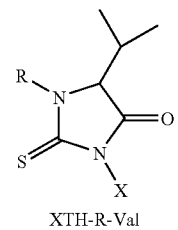

XTH-R-Val

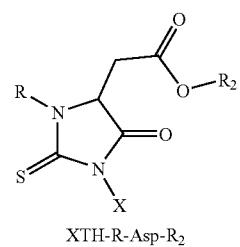

XTH-R-Asp-R$_2$ wherein R represents any adduct (e.g., alkyl and aryl or substituted analogues thereof, with the exception of hydrogen) and X represents a moiety of any isothiocyanate reagent utilized in which the isothiocyanate group is directly bound to an aromatic ring or an aromatic ring system, thereby providing fluorescent and/or ionizable properties to the analyte, with the exception that X is not a phenyl, 4-bromophenyl, 4-methoxyphenyl or pentafluorophenyl group; and R$_2$ represents hydrogen, alkyl, aryl, carboxyl, benzyl or substituted analogues thereof, or a carboxyl anion group.

According to a preferred embodiment of the second aspect of the invention, said analyte is a compound selected from the group of 3-[4-(4-dimethylamino-phenylazo)-phenyl]-5-isopropyl-1-methyl-2-thioxo-imidazolidin-4-one (DABTH-MeVal); 3-(4-dimethylamino-naphthalen-1-yl)-5-isopropyl-1-methyl-2-thioxo-imidazolidin-4-one (DNTH-MeVal); fluorescein, 5-(4-isopropyl-3-methyl-2-thioxo-imidazolidin-5-one) (FTH-MeVal); fluorescein, 5-[4-isopropyl-3-(2-carbamoyl-ethyl)-2-thioxo-imidazolidin-5-one] (FTH-AAVal); fluorescein, 5-[4-isopropyl-3-(2-carbamoyl-2-hydroxy-ethyl)-2-thioxo-imidazolidin-5-one] (FTH-GAVal); fluorescein, 5-[4-isopropyl-3-(2-hydroxyoctadecyl)-2-thioxo-imidazolidin-5-one] (FTH-HOC$_{18}$Val); fluorescein, 5-[4-isopropyl-3-(2-hydroxy-propyl)-2-thioxo-imidazolidin-5-one] (FTH-HOPrVal); fluorescein, 5-{4-isopropyl-3-[17-(1,5-dimethyl-hexyl)-3,5 and/or 6-dihydroxy-10,13-dimethyl-hexadecahydro-cyclopenta[a]phenanthren-5 and/or 6-yl])-2-thioxo-imidazolidin-5-one} (FTH-CholEOVal) and fluorescein, 5-[4-isopropyl-3-(2,3,4,5,6-pentahydroxy-hexyl)-2-thioxo-imidazolidin-5-one] (FTH-GlcVal).

According to a preferred embodiment of the seventh aspect of the invention, said kit consists of standard material according to the third aspect of the present invention or a compound according to the fourth aspect, and a container according to the sixth aspect of the present invention.

The method according to the first aspect of the present invention accordingly utilizes isothiocyanate reagents with, preferably, ionizable functional groups, e.g., carboxyl groups and tertiary amines, in order to:

a) simplify the clean-up, e.g., by enrichment of the analytes using of ion-exchangers.

b) be able to utilize highly effective separation techniques such as electrophoresis; e.g., capillary electrophoresis (CE) and liquid chromatography (LC);
c) utilize ionizable groups for altering the solubilites of reagents/analytes by changing the pH to above or below their $pK_a$ values. For example, the carboxyl group in FITC provides the reagent (and analytes formed) with increased water solubility at the pH for the coupling reaction (see FIG. 3) as well as excellent chromatographic properties for separation on LC systems using buffered mobile phases with pH values 2-3 pH units below the $pK_a$ of the analytes. This same principle is also utilized for enrichment by solid phase extraction (SPE), e.g., FTH-R-valines are bound to SPE (e.g., non-polar C-18 gels) under acidic conditions and released by alkalization or the use of non-polar solvents;
d) provide high sensitivities and low limit of detection (LOD) when using mass spectrometric (MS) detection techniques, e.g., LC-MS, due to more effective ionization of the analytes.

The method according to the first aspect of the present invention accordingly utilizes isothiocyanate reagents that form thiohydantoines analytes which are fluorescent, making it possible to utilize a wider range of analytical separation and detection techniques, e.g.:
a) capillary electrophoresis with laser-induced fluorescence detection (CE-LIF). This approach will give the benefit of a very high sensitivity and moderate-to-high selectivity, in accordance with Irland et al. (19), who separated 18 of 20 coded FTH-amino acids formed according to the original Edman method (8) and analyzed these with a LOD (limit of detection) of about 10 zmol ($10^{-21}$);
b) LC separation using laser-induced fluorescence detection (LC-LIF);
c) CE or LC with fluorescence detection. These systems are very common, easy to operate, provide good sensitivity and are relatively inexpensive.
d) CE or LC with UV detection, e.g., CE using a diode array UV detector (DAD). These types of systems provide some selectivity, good reproducibility and fair sensitivity and are easy to operate.
e) LC separation using fluorescence detection combined with MS detection. This approach will give the benefits of both of these techniques, possessing both high sensitivity and specificity. This is a powerful tool for identification and determination of previously unknown adducts, as well as low levels of adducts (near the lower LOD);
f) gel electrophoresis with fluorescence detection. This approach will give the benefit of high sensitivity and moderate-to-high resolution when separated multi-dimensional and provides the possibility of running samples in parallel with possibility for repeated scans for increased sensitivity;
g) capillary electrophoresis with application of analytes on a rotating device followed by fluorescence detection. This approach will combine the benefit of high separation efficiency with the possibility for performing repeated scans for increased sensitivity.

In addition to the above-mentioned advantages provided by the different instrumental combinations, these techniques demonstrate good linearity of quantification. The method according to the first aspect of the present invention provides thereby new possibilities for quantification in comparison with the GC-optimized N-alkyl Edman procedure The mild and non-discriminating conditions utilized in the method according to the first aspect of the present invention increase its range of applicability in comparison to presently existing methods for measurement of N-terminal protein adducts. This new method should be powerful enough for routine analysis for hygienic and environmental surveillance, medical purposes, and animal studies and for analysis of controlled substances that form electrophilically reactive metabolites in vivo.

In comparison to the 'N-alkyl Edman procedure', utilization of the method according to the first aspect of the present invention makes it possible, as shown by the experimental results, presented below, to;
1) increase the range of adducts to be analyzed, e.g.,
   a) high-molecular weight adducts (>500 mu), as well as adducts with low molecular weights can be readily analyzed using, e.g., LC and CE;
   b) very polar-to-non-polar adducts can be analyzed using, e.g., LC and CE;
   c) Thermo-labile adducts can be analyzed using, e.g., LC and CE;
2) increase the types of separation techniques that be employed for adduct analysis,
3) improve and speed-up sample clean-up and extraction;
4) improve the sensitivity of detection of the analytes using, e.g., LC-MS/MS and LIF.

The preferred features of each aspect of the invention are, as for each of the other aspects, mutatis mutandis. The prior art documents mentioned herein are incorporated to the fullest extent permitted by law. The invention is further described in the following examples, in conjunction with the appended figures, which do not in any way limit the scope of the invention. Embodiments of the present invention are described in more detail with the aid of examples of embodiments and figures, the only purpose of which is to illustrate the invention and are in no way intended to limit the range of its applicability.

SHORT DESCRIPTION OF THE FIGURES

FIG. 1 presents a brief description of the N-alkyl Edman procedure, i.e. the traditional method for determination of adducts by GC-MS/MS.

FIG. 2 depicts the principles of the method according to the first aspect of the present invention, i.e., the present method.

FIG. 3 shows the reactions and the reagents studied: Three selected fluorescent/ionizable isothiocyanate reagents, i.e., fluorescein isothiocyanate (FITC), 4-N,N-dimethylaminoazobenzene 4'-isothiocyanate (DABITC) and 4-dimethylamino-1-naphthyl isothiocyanate (DNITC), used in the method described in the first aspect of the present invention were compared with the two reagents, phenyl isothiocyanate (PITC) and pentafluorophenyl isothiocyanate (PFPITC), used in the N-alkyl Edman procedure.

FIG. 4 illustrates the general structures of analytes and proposed analytes formed with the method described in the first aspect of the present invention from adducted valine or asparagine as free amino acids or N-terminals in peptides/proteins.

FIG. 5 shows the structures of compounds 1-16 as taken as examples of the present description.

FIG. 6 presents a complete baseline separation obtained with CE.

FIGS. 7-11 depicts the results from fluorescence measurements.

FIGS. 12-13 illustrates the UV absorbance of selected analytes, using fluoranthene as a reference.

FIG. 14 shows an LC-MS/MS analysis of acrylamide-adducted human globin by the method described in the first aspect of the present invention in comparison to reference compounds.

FIG. 15 presents excitation and emission spectra of FTH-MeVal (10).

FIG. 16 shows an LC-MS/MS analysis of FTH-GlcVal (16) formed from human globin N-glykosylated in vivo using the method described in the first aspect of the present invention in comparison to reference compounds.

FIGS. 17-18. Depicts a comparison of the relative sensitivities (presented on a log scale) obtained from determination of the limits of detection (LOD) with LC-MS/MS in the ESI and APCI modes.

FIG. 19. Illustration a simplified approach to sample preparation and clean-up based on the principles of the fluorescent/ionizable N-R-Edman procedure of the first aspect of the present invention.

EXAMPLES

The method according to the first aspect of the present invention has been studied and evaluated utilizing three isothiocyanate reagents, i.e., fluorescein-5-isothiocyanate (FITC), 4'-N,N-dimethylaminoazobenzene-4-isothiocyanate (DABITC) and 4-dimethylamino-1-isothiocyanate (DNITC), that all form fluorescent thiohydantoines directly with N-substituted valines, valylpeptides (N-methylated) and proteins (human globin, alkylated with several alkylating agents was tested). These analytes were then compared with the reagents employed in the GC-based N-alkyl Edman procedure, PITC and pentafluorophenyl isothiocyanate (PF-PITC). In this context, PITC has recently been applied for LC-MS/MS analysis of acrylamide and glycidamide adducts of hemoglobin (20). For comparison between alkylated and non-alkylated analytes, normal valine and valyl peptides were reacted with the isothiocyanate reagents selected. However, in order to form thiohydantoines from unsubstituted valine/valyl peptides, an additional acidification step must be performed in accordance with the principles of the traditional Edman degradation reaction (8). The reactions and reagents studied are summarized in FIG. 3 and the structures and abbreviations of the analytes synthesized are shown in FIG. 5.

Selected methylated and non-methylated analytes, (1,2; 5,6; 7,8 and 9, 10) were then measured at various pH's on different analytical techniques, i.e., ultraviolet-visible spectroscopy (UV/vis), HPLC, LC-MS and LC-MS/MS. The fluorescent analytes were also analysed by fluorescence spectroscopy (to obtain excitation and emission spectra) and by CE with diode array detection. It was observed that one of the fluorescent reagents tested was particularly well suited for analysis with these techniques.

Thus, FITC was selected for further studies using alkylated model peptides and globin adducted with acrylamide (11), glycidamide (12), 2-octadecyl-oxirane (13), propylene oxide (14), cholesterol-5α,6α-epoxide, (15) and reductively aminated glucose (16). These analytes (11-16, FIG. 5) were analysed by LC-MS/MS (ESI, electrospray ionization) and shown to give good response in the system applied. These analytes (11-16), formed by coupling/detachment with FITC from globin alkylated in vitro, were isolated by size-discriminating ultrafiltration (MWCO 5,000 or 10,000) or by protein precipitation (e.g., with ethanol or acetonitrile), followed by anion exchange, e.g., on solid phase extraction column. The isolated extracts were then directly and successfully analyzed by LC-MS/MS with high sensitivity (e.g., FIGS. 14 and 16). In this context, analytes were also measured according to simplified approach to sample preparation (FIG. 19). Data on the sensitivity (expressed as the limit of detection, LOD) for the reagents tested and the corresponding methylated and non-methylated thiohydantoines are presented in Table 1. FTH-MeVal (10) was found to provide 600-16,000 fold higher molar sensitivity than PTH-MeVal (1). It was found that all three model reagents selected for the method according to the first aspect, i.e., FITC, DABITC and DNITC, react and detach the adduct moieties with high selectively. These reagents thus gave consequentially much lower LODs compared to the reagents utilized in the usual N-alkyl Edman procedure, e.g., as low as 2.6 fmol ($2.6 \times 10^{-15}$ moles) for fluorescein N-methylvaline thiohydantoin (FTH-MeVal, 10, Table 1) with the LC-MS/MS methods employed for analysis. This high sensitivity, reflected as lower LODs, is probably a result of the ionizable groups incorporated into the reagents, which are ionized to a higher degree in the MS instrument than are adducted PTH and PFPTH analytes without ionizable groups.

In order to evaluate the possibility of measuring N-terminal adducts with such sensitive techniques as CE-LIF, the fluorescent analytes 5-10 were also characterized with fluorescence spectroscopy (excitation and emission spectra) and analyzed by CE with a diode array detector (UV). With FTH-Val (9) and FTH-MeVal (10), complete baseline separation was obtained (FIG. 6).

The studies on the relative fluorescence of the fluorescent analytes (compound 5-10) involved determination of the excitation and emission spectra. The results, presented in FIGS. 7-11, show that FTH-MeVal (10) gave a detectable response even at the lowest concentration tested. FTH-MeVal (10) was detected at a concentration 360-fold lower than the detectible concentration of fluoranthene, which was used as a reference, and at concentrations 45-fold lower than DABTH-MeVal (6) and 530-fold lower than DNTH-MeVal (8). The excitation and emission spectra were measured at wavelengths and a pH suitable for each compound.

Experimental

Material and Methods

The structures of compounds 1-16 are given in FIG. 5. Fluoresceine-5-isothiocyanate (isomer I, <90%), sodium cyanoborohydride, pentafluorophenyl isothiocyanate (PF-PITC) and phenyl isothiocyanate (PITC, purum) (Fluka); 4-N,N-dimethylaminoazobenzene 4'-isothiocyanate (DABITC) and 4-dimethylamino-1-naphthyl isothiocyanate (DNITC) (Acros); cholesterol-5α,6α-epoxide, D-glucose, horse skeletal myoglobin, octadecyl-epoxide, L-valine (Val), L-valylleucin (ValLeu), N-methyl-D,L-valine (MeVal), 5-isopropyl-3-phenyl-2-thiohydantoin (1, Val-PTH) and sodium borohydride phosphate buffer (Sigma); N-methylvalylleucylanilide (MeValLeu-NHφ, >99%) and valylleucylserine (ValLeuSer (H-Val-Leu-Ser-OH) 95%) (Bachem, Bubendorf, Switzerland) and ($^2H_3$) acetonitrile (99.8% $^2H$), ($^2H$) chloroform (99.8% $^2H$), deuterium oxide (99.9% $^2H$, $^2H_2O$), and ($^2H_4$) methanol (99.8% $^2H$) (CIL, Andover, Mass.) were all obtained from the sources indicated. 5-Isopropyl-1-methyl-3-phenyl-2-thiohydantoin (2, PTH-MeVal), 5-isopropyl-3-pentafluorophenyl-2-valinethiohydantoin (3, PFPTH-MeVal) and 1-hydroxyethyl-5-isopropyl-3-pentafluorophenyl-2-thiohydantoin (4, PFPTH-HOEtVal) were synthesized as described earlier (21). Glycidamide (GA) was synthesized from acrylonitrile according to method B of Payne and Williams (22). All other chemicals and solvents were of analytical grade.

The size-discriminating ultrafiltration tubes "Vivaspin 6" and "Centrisart I; 5000 and 10000 MWCO" were obtained from Sartorius AG (Hanover, Germany) and the ion-exchanger, Amberlyst A-26, from BHD Chemicals Ltd (Poole, England).

Instrumentation, Methods for Analysis and Characterization.

$^1$H and $^{13}$C NMR spectra were recorded on a JEOL GSX 270 instrument at 270 MHz. All solvents used were fully deuterated; TMS dissolved in chloroform, acetonitrile and methanol was added as internal standard.

The absorbance spectra of the reagents investigated were obtained in water:acetonitrile solutions (1:1) with no buffer added and in 0.1% TFA, using a double-beam Hitachi U3000 UV spectrophotometer, scanning from 200-600 nm. Quartz cuvettes (10 mm) were used.

Fluorescence excitation and emission spectra were recorded in water:acetonitrile solutions (2:1) at various pHs (between 1 and 9) using a Schimadzu RF5000 fluorescence spectrophotometer. Emission was scanned from 10 nm above the excitation wavelength, locked at the optimal absorbance wavelength determined from the UV absorbance measurements described above, to 600 nm. Excitation was then scanned from 200 nm to 10 nm below the emission wavelength locked at the optimal wavelength obtained during the emission scan. Emission and excitation spectra for the analytes were compared with the same instrumental settings (slit 5) and using a pH suitable for each analyte. A quartz cuvette (10 mm) was used.

TLC was performed using silica gel 60 f-254 plates ($SiO_2$, Merck) and the spots developed with both UV (254 nm) and at long wavelength (378 nm). Melting points were determined on a Büchi 535 instrument. Measurements of pH were carried out on an Orion EA 920 pH-meter equipped with a Ross 8130 glass electrode.

Studies on the retention times of compounds 5-10 were performed using a Shimadzu LC-4A (Kyoto, Japan) HPLC with a Shimadzu SPD-2AS UV detector ($\lambda$=268 nm, $D_2$ lamp). The separation column was a Kromasil LC-18 column (250×10 mm) and the flow-rate was 2.5 mL/min, with a sample loop of 0.7 mL. The mobile phase consisted of water buffered with 0.02% TFA and acetonitrile. A gradient was applied starting with 5% acetonitrile to a final composition of 80% acetonitrile. The LC-MS system consisted of a Rheos 4000LC pump (Flux Instruments, Basel, Switzerland) interfaced with a LCQ MS (ThermoQuest, CA, USA). Well adapted buffer systems, e.g., 0.1% TFA, 0.1% ammonium acetate and 0.3 mM aqueous ammonia, were used. For the determination of the LOD, the flow rate of the aqueous buffer/acetonitrile [1:1 (v/v)] was 200 µL/min and the analytes were dissolved in the same buffers and solvent mixtures at concentrations ranging from 10 µg/mL down to 1 ng/mL, depending on their response and the operating conditions. The injection volume was 5 µL (n=3 for each compound). Nitrogen gas was used for drying at a flow-rate of 250 L/h. Both the positive- and negative-ion modes were used. Determinations in the MS-MS mode were performed by collision-induced dissociation (CID) of the [M+1] ion. When MS was carried out in the electrospray ionization (ESI) mode, the mobile phase consisted of H2O:acetonitrile (1:1) with an isocratic flow-rate of 200 µL/min. The ion-source temperature was 120° C., the capillary temperature 250° C., the capillary voltage 10 V. Nitrogen was used as the sheath gas and the cone voltage varied between 25 and 140 V in order to obtain maximum sensitivity for each specific analyte. When operating in the atmospheric pressure-chemical ionization (APCI) mode, the following conditions were employed: The mobile phase consisted of $H_2O$:acetonitrile (1:1) with an isocratic flow-rate of 500 µL/min. The vaporizing temperature was 450° C., the capillary temperature 150° C., the capillary voltage of 5 V and nitrogen was used as the sheath gas.

The CE separation was performed on an HP 3D CE column (Agilent, Calif., USA) with a five-channel diode array UV detector. A fused silica capillary (i.d. 50 µm, o.d. 375 µm) with a total length of 64 cm and an effective length of 56 cm was used. The separation voltage was +30 kV, resulting in a separation current of 32 µA. The buffer system consisted of 17 mM phosphate buffer (adjusted to pH 7) containing 20 mM SDS and the injection volume was 1 nL.

Synthesis of Reference Compounds/Analytes

Synthesis of 3-[4-(4-dimethylamino-phenylazo)-phenyl]-5-isopropyl-2-thioxo-imidazolidin-4-one (5, DABTH-Val). From a stock solution of 0.500 M L-valine (20 mmol in 40 ml 0.25 M KOH), a 5.0-mL aliquot (2.5 mmol Val) was heated to 60° C. and mixed with 5.0 ml 0.10 M 4-N,N-dimethylaminoazobenzene 4'-isothiocyanate (DABITC, 0.5 mmol) in dioxane. In order to obtain a homogeneous solution, an additional 3.5 mL dioxane and 2.5 mL water were added. The reaction was monitored by TLC (EtOAc/MeOH, 4:1) and after 30 min the reagent, DABITC, had been consumed. Concentrated HCl (1 mL, 12 mM) was added in order to convert the 4-N,N-dimethylaminoazobenzene 4'-thiocarbamoyl-valine formed to the corresponding ring-closed DABTH-Val (5). This reaction was also monitored by TLC (Tol:EtOAc, 2:1; spots developed with both UV and long wavelength light) and found to be complete after 30 min at 60° C. The solution was then extracted with chloroform (25 mL) and water (25 mL), the aqueous phase thus obtained neutralized with $KHCO_3$, and the product then extracted from this phase with chloroform (2×25 mL). This chloroform phase was subsequently extracted with water (25 mL) and the solution dried with $Na_2SO_4$. After filtration and evaporation, the orange-colored solid obtained was crystallized from DCM:hexane (2:1) to yield 131.7 mg (69.0%) of the described product. Analysis: m.p. 225° C. Rf-TLC 0.73 (EtOAc:MeOH, 4:1). UV (acetonitrile:water, 1:1) $\lambda_{max}$=265 nm, $\epsilon_{265}$=28000 (see also FIG. 13). $^1$H NMR (CDCl$_3$, 25° C.) δ1.06, 1.15[d+d, 3+3H, J=6.9, 7.1 Hz, CH$_3$(γ,γ')], 2.39 [m, 1H, J=3.3, 6.9, 7.1 Hz, CH(β)], 3.09 [s, 6H, N(CH$_3$)$_2$] 4.18 [d, 1H, J=3.3, CH(α)], 6.75, 6.77 [d+d, 2H, azobenzene C$_6$—H, C$_7$—H] 7.39, 7.41 [d+d, 2H, azobenzene C$_5$—H, C$_8$—H] 7.88, 7.90, 7.94, 7.96 [4d, 4H, azobenzene C$_1$—H—C$_4$—H].

Synthesis of 3-[4-(4-dimethylamino-phenylazo)-phenyl]-5-isopropyl-1-methyl-2-thioxo-imidazolidin-4-one (6, DABTH-MeVal). From a stock solution of 0.500 M N-(Me)-D,L-valine (20 mmol in 40 mL 0.25 M KOH), a 5.0-mL aliquot (2.5 mmol MeVal) was heated to 60° C. and mixed with 0.100M DABITC (5.0 mL, 0.5 mmol) in dioxane. In order to obtain a homogeneous solution another 3.5 mL dioxane and 2.5 mL water were added. This reaction mixture became inhomogeneous in contrast to the mixture containing Val, indicating that the DABTH-MeVal formed precipitated. The reaction was monitored by TLC (SiO$_2$ Tol/EtOAc, 2:1; spots developed with both UV and long wavelength light) and after 30 min all the DABITC had been consumed. The subsequent extraction was performed as described above. The product crystallized from DCM:hexane (1:4, v/v) to yield 189.0 mg (99.5%) of the desired product. Analysis: m.p. 164.5-169° C., Rf-TLC 0.73 (SiO$_2$; EtOAc:MeOH, 4:1). UV (acetonitrile:water 1:1) $\lambda_{max}$=265 nm, $\epsilon_{265}$=26000 (see also FIG. 12). Fluorescence measurements: see FIGS. 9 and 10. $^1$H NMR(CDCl$_3$, 25° C.) δ1.05, 1.25[d+d, 3+3H, J=6.9, 7.1 Hz, CH$_3$(γ,γ')], 2.47 [m, 1H, J=3.3, 6.9, 7.1 Hz, CH(β)], 3.09

[s, 6H, N(CH$_3$)$_2$] 3.4[s, 3H, N—CH$_3$], 4.4 [d, 1H, J=3.3 Hz, CH($\alpha$)], 6.74, 6.77 [d+d, 2H, azobenzene C$_6$—H, C$_7$—H] 7.37, 7.40 [d+d, 2H, azobenzene C$_5$—H, C$_8$—H] 7.87, 7.90, 7.92, 7.95 [4d, 4H, azobenzene C$_1$—H—C$_4$—H].

Synthesis of 3-(4-dimethylamino-naphthalen-1-yl)-5-isopropyl-2-thioxo-imidazolidin-4-one (7, DNTH-Val). L-Valine (804 mg=6.86 mmol) was alkalized with KOH (3.43 mmol) and dissolved in 0.5 M KHCO$_3$ (3 mL) and dioxane (3 mL). This solution was heated to 45° C. with magnetic stirring and DNITC (88 mg, 0.385 mmol) dissolved in dioxane (2 mL) was added to the suspension. The reaction was monitored by TLC (SiO$_2$; ethyl acetate/MeOH, 4:1, toluene and toluene/ethyl acetate, 2:1) using a reference without valine. After 60 min the reaction was in principle complete, since no DNITC could be detected by TLC and the product formed, i.e., the 4-Me$_2$N-naphthyl-thiocarbamoyl-valinate, gave fluorescence at long wavelength under the UV lamp (seen as a tailing spot on TLC eluted with ethyl acetate/MeOH, 4:1). The reaction mixture was acidified with 3 mL concentrated hydrochloric acid (36 mmol) after 2 h at 45° C., this reaction was stopped by neutralization by addition of solid KHCO$_3$ until no more carbon dioxide was released. Thereafter the reaction mixture was diluted with water (100 mL) and the product purified by extraction with CHCl$_3$ (125 ml). The organic phase was dried with Na$_2$SO$_4$, filtered and the solvent removed by evaporation to yield 126 mg (96%) of the desired product as a white solid. Analysis: m.p. 107.5-110° C. Rf-TLC 0.73 (EtOAc:MeOH, 4:1). UV (acetonitrile:water, 1:1) $\lambda_{max}$=260 nm, $\epsilon_{260}$=21000 (see also FIGS. 12 and 13). $^1$H NMR ($^2$H$_6$-acetone, 25° C.) $\delta$1.10, 1.25[d+d, 3+3H, J=6.9, 7.1 Hz, CH$_3$($\gamma,\gamma'$) assigned to the thiohydantoin], 1.17-1.21 [d+d, 3+3H, J=6.9 Hz, CH$_3$($\gamma,\gamma'$) assigned to the thiocarbamoyl], 2.40 [m, 1H, J=3.8, 6.9 Hz, CH($\beta$)], 2.92 [s, 6H, N(CH$_3$)$_2$] 4.45, 4.56 [d+d, 1H, J=1.65, 3.85 Hz, CH($\alpha$)], 7.17-8.32 [m, 6H, naphthalene-H]. $^{13}$C NMR (acetone, 25° C.) $\delta$ 16.8, 17.4; 18.7, 19.0 [2×CH$_3$($\gamma,\gamma'$)], 31.66; 32.0 [2×CH ($\beta$)], 45.4 [N—(CH$_3$)$_2$], 65.7; 66.1 [2×CH($\alpha$)], 114-153 [naphthalene], 174.9 [CO], 185.8; 185.9 [2×CS]. This molecule was found to be partly hydrolyzed to the corresponding ring-opened thiocarbamoyl compound. All shifts obtained are presented, but not assigned to the individual compounds.

Synthesis of 3-(4-dimethylamino-naphthalen-1-yl)-5-isopropyl-1-methyl-2-thioxo-imidazolidin-4-one (8, DNTH-MeVal). D,L-MeVal (93.0 mg, 0.708 mmol; prepared according to Rydberg et al. 1993) was alkalized with KOH (0.4 mmol) and dissolved in 0.5 M KHCO$_3$ (3 mL) and dioxane (2 mL). This solution was heated to 45° C. with magnetic stirring and 4-dimethylnaphthylisothiocyanate (DNITC, 91.3 mg, 0.40 mmol) dissolved in dioxane (2 mL) then added. The reaction was monitored by TLC (SiO$_2$; toluene and toluene/ethylacetate, 2:1) using a reference without MeVal. After 60 min, the reagent DNITC had been consumed and following TLC elution with toluene/ethylacetate, the analyte formed could be visualized on the basis of its fluorescence at long wavelength under the UV lamp. The reaction mixture was extracted with toluene and purified by column chromatography (SiO$_2$) eluted with toluene/ethyl acetate (2:1) to yield 130 mg (96%) of the desired product. This product was crystallized from ethanol/water (1:1), to yield white crystals (100 mg, 73%) with the following characteristics: m.p. 157-159° C. Rf-TLC 0.72 (EtOAc:MeOH, 4:1), UV (acetonitrile:water 1:1) $\lambda_{max}$=260 nm, $\epsilon_{260}$=21000 (see also FIGS. 12 and 13). Fluorescence measurements: see FIG. 10. $^1$H NMR ($^2$H$_6$-acetone, 25° C.) $\delta$1.04, 1.16[d+d, 3+3H, J=6.9, 7.1 Hz, CH$_3$ ($\gamma,\gamma'$) assigned to the thiohydantoin], 1.24, 1.28[d+d, 3+3H, J=6.9 Hz, CH$_3$($\gamma,\gamma'$) assigned to the thiocarbamoyl], 2.59 [m, 1H, J=3.3, 6.9, 7.1 Hz, CH($\beta$)], 2.92 [s, 6H, N(CH$_3$)$_2$] 3.41, [d, 3H, J=1.65, Hz, N—CH$_3$] 4.38, 4.50 [d+d, 1H, J=3.0, 3.3 Hz, CH($\alpha$)], 7.15-8.31 [m, 6H, naphthalene-H]. $^{13}$C NMR (acetone, 25° C.) $\delta$ 16.3, 17.1; 17.5, 17.8 [2×CH$_3$($\gamma,\gamma'$)], 30.3 [CH($\beta$)], 33.0; 33.1 [2×N—CH$_3$], 45.4 [N—(CH$_3$)$_2$], $\delta$69.1; 69.4 [2×CH($\alpha$)], 114-153 [2× naphthalene], 173.5 [CO], 184.3; 184.4 [2×CS]. This molecule was found to be partially hydrolyzed to the corresponding ring-opened thiocarbamoyl compound. All shifts obtained are presented, but not assigned to individual compounds.

Synthesis of fluorescein, 5-(4-isopropyl-2-thioxo-imidazolidin-5-one) (9, FTH-Val).

From a stock solution of 0,500 M L-valine (20 mmol in 40 ml 0.25 M KOH), a 5.0-mL aliquot (2.5 mmol Val) was heated to 45° C. and then reacted with FITC (0.50 mmol, 199 mg) dissolved in 6 mL dioxane/water (10:1). The reaction was followed by TLC and after 90 min, all of the FITC had been consumed. Concentrated HCl (1 mL, 12 mM) was added in order to convert the 5-fluorescein thiocarbamoyl-valinate formed to the correspondingly ring-closed FTH-Val, a reaction which was completed after 14 h at 45° C. The solvent was evaporated under vacuum and the dry solid remaining dissolved in water:EtOAc (1:1, total volume 60 mL). The EtOAc phase was extracted with water (15 mL×2). The combined aqueous phases were then extracted with EtOAc (20 mL) and combined with the first EtOAc phase, which was finally extracted with water (2×15 mL). The organic phase was dried with Na$_2$SO$_4$ and the product dissolved in EtOAc:MeOH (4:1) and purified by column chromatography (SiO$_2$, 25×3 cm) eluted with EtOAc:MeOH (4:1). The fractions containing the products were combined, dried by evaporation and crystallized from EtOH:water (1:1) to yield 167 mg (68.4%) of the desired product. Analysis: m.p. 232.5-234.5° C. Rf-TLC 0.65 (EtOAc:MeOH, 4:1). UV (aetonitrile:water 1:1) $\lambda_{max}$=268 nm, $\epsilon_{268}$=21500 (see also FIGS. 12 and 13). Fluorescence measurements: see FIGS. 7 and 10). $^1$H NMR (acetone, 25° C.) $\delta$1.08, 1.18[d+d, 3+3H, J=6.9, 6.6 Hz, CH$_3$($\gamma,\gamma'$)], 2.38 [m, 1H, J=3.8, 6.9 Hz, CH($\beta$)], 2.86 [s, 1H, not assigned] 4.4[d, 1H, J=3.8 Hz, CH($\alpha$)], 6.66-6.77 [6H, m with the most pronounced peak at 6.71, xanthene-H], 7.39, 7.42 [d+d, 1H, J=0.55, 8.2 Hz, C$_7$—H] 7.74, 7.77 [d+d, 1H, J=1.9, 8.2 Hz, C$_6$—H], 7.96 [d, 1H, J=1.6 Hz, C$_4$—H] 9.0 [s, 2H, xanthene-(OH)$_2$] 9.5 [s, 1H, N—H]. $^{13}$C NMR (acetone, CD$_3$OD, 25° C.) $\delta$ 17.0, 18.9 [CH$_3$($\gamma,\gamma'$)], 32.5 [CH($\beta$)], 66.3 [CH($\alpha$)], 103.7, 113.8, 125.9, 126.1, 130.5, 154.0, 161.3 [xanthene carbons], 136.5, 136.9 [C$_2$+C$_5$], 169.9 [COO], 175.2 [CO], 184.6 [CS]. The chemical shifts of five of the carbon atoms are not given, (impossible to separate from the background noise). However, the presented carbons were in accordance with the predicted shifts of compound 9 in its assumed spiro-conformation (see FIG. 3).

Synthesis of fluorescein, 5-(4-isopropyl-3-methyl-2-thioxo-imidazolidin-5-one) (10, FTH-MeVal). From a stock solution of 0,500 M N-(Me)-D,L-valine (20 mmol in 40 ml 0.25 M KOH), a 5.0-mL aliquot (2.5 mmol MeVal) was heated to 45° C. and then reacted with FITC (0.50 mmol, 199 mg) dissolved in 6 mL dioxane/water (10:1). This reaction was monitored by TLC and after 90 min, all of the FITC had been consumed. In order to extract the product formed, the solution containing FTH-MeVal was acidified with concentrated HCl (1 mL, 12 mM) and extracted as described above. After evaporation to dryness the product was purified by column chromatography and crystallized as described above to yield 194.4 mg (77.4%) of the desired product. Analysis: m.p. 213.5-217° C. Rf-TLC 0.64 (EtOAc:MeOH, 4:1). UV (acetonitrile:water, 1:1) $\lambda$max=268 nm, $\epsilon_{268}$=17500 (see also FIGS. 12 and 13). Fluorescence measurements: see FIGS. 8 and 10. $^1$H NMR (acetone, 25° C.) $\delta$1.01, 1.25[d+d, 3+3H, J=6.9 Hz, CH$_3$(γ,γ')], 2.57 [m, 1H, J=3.6, 6.9 Hz, CH(β)], 2.87 [s, 1H, not assigned] 3.4[s, 3H, N—CH$_3$], 4.4[d, 1H, J=3.0 Hz, CH(α)], 6.65-6.77 [6H, m with the most pronounced peak at 6.71, xanthene-H], 7.39, 7.42 [d+d, 1H, J=0.55, 8.2 Hz, C$_7$—H] 7.72, 7.75 [d+d, 1H, J=1.9, 8.2 Hz, C$_6$—H], 7.93 [d, 1H, J=1.9 Hz, C$_4$—H] 9.0 [s, 2H, xanthene-(OH)$_2$]. $^{13}$C NMR (acetone, 25° C.) δ 16.3, 17.5 [CH$_3$(γ,γ')], 30.3 [CH(β)], 33.1 [N—CH$_3$], 69.3[CH(α)], 103.5, 113.5, 125.4, 125.7, 130.2, 153.4, 153.8, 160.5 [xanthene carbons] 136.6 [C$_2$ or C$_5$], 168.7 [COO], 172.7 [CO], 182.7 [CS]. The chemical shifts of six of the carbon atoms are not given, (impossible to separate from the background noise), however, the presented carbons shifts were in accordance to the predicted shifts for compound 10 in its assumed spiro-conformation (see FIG. 3).

Synthesis of fluorescein, 5-[4-isopropyl-3-(2-carbamoyl-ethyl)-2-thioxo-imidazolidin-5-one] (11, FTH-AAVal). Valine (117 mg, 1.0 mol) was dissolved in 10 mL water/dioxane (4:1) and the pH of this solution adjusted to approximately 10 by addition of NaOH (20 mg, 0.50 mmol). To this solution acrylamide (71 mg, 1.0 mmol) was added and thereafter the solution was heated at 45° C. for three days. An aliquot of this mixture (2.5 mL, containing 0.25 mmol reacted valine) was then reacted directly with FITC (20 mg, 0.051 mmol) at 60° C. for 90 min. Subsequently, this reaction mixture was acidified with 0.5 mL 1 M HCl (0.50 mmol); the product re-dissolved and extracted in water (10 mL) and EtOAc (10 mL); the EtOAc phase extracted with another two volumes of water (10 mL). The EtOAc phase was dried with Na$_2$SO$_4$ and then evaporated to dryness to yield FTH-AAVal (25 mg, 0.046 mmol; 90%) containing small amounts of impurities, as revealed by TLC (SiO$_2$; EtOAc:MeOH, 4:1). Characterization was performed by LC-MS (ESI) in both the positive and negative modes.

In vitro alkylation of globin with glycidamide, octadecyl-1.2-epoxide, propylene oxide and cholesterol-5α,6α-epoxide.

The general procedure employed was as follows: Four portions of globin (50 mg), isolated from hemoglobin according to Mowrer et al. (23) were dissolved in 2 mL 0.5 M aqueous KHCO$_3$:2-propanol (2:1) and then alkylated with glycidamide (10 mg, 0.11 mmol), octadecyl epoxide (10 mg, 0.037 mmol), propylene oxide (10 mg, 0.17 mmol) or cholesterole-5α,6α-epoxide (10 mg, 0.025 mmol). Additional 1-mL portions of dioxan were added in order to make the samples containing octadecyl epoxide and cholesterol-5α,6α-epoxide homogenous. These reaction mixtures were maintained at 60° C. for three days, and the product purified from the excess alkylating reagents and from by products by use of size-discriminating ultrafiltration. The alkylated globins thus obtained were re-dissolved and derivatised with FITC as described below.

FITC derivatisation of alkylated globins and analysis of the FTH derivatives formed: fluorescein, 5-[4-isopropyl-3-(2-carbamoyl-ethyl)-2-thioxo-imidazolidin-5-one](FTH-AAVal); fluorescein, 5-[4-isopropyl-3-(2-carbamoyl-2-hydroxy-ethyl)-2-thioxo-imidazolidin-5-one](FTH-GA Val); fluorescein, 5-[4-isopropyl-3-(2-hydroxy-octadecyl)-2-thioxo-imidazolidin-5-one] (FTH-HOC$_{18}$Val); fluorescein, 5-[4-isopropyl-3-(2-hydroxy-propyl)-2-thioxo-imidazolidin-5-one] (FTH-HOPrVal) and fluorescein, 5-{4-isopropyl-3-[17-(1,5-dimethyl-hexyl)-3,5 and/or 6-dihydroxy-10,13-dimethyl-hexadecahydro-cyclopenta[a]phenanthren-5 and/or 6-yl])-2-thioxo-imidazolidin-5-one} (FTH-CholEOVal).

The alkylated globin samples described above (n=4), i.e., globin alkylated with acrylamide (50 mg, 7-10 nmol acrylamide/g globin, gift from Birgit Paulsson) together with one control globin (50 mg normal globin) and one control myoglobin (50 mg horse skeletal myoglobin) sample, were dissolved separately in 2 mL 0.5 M aqueous KHCO$_3$: 2-propanol (2:1) and reacted with FITC (15 mg, 0.038 mmol). After 90 min at 60° C., the reaction mixtures were diluted with 2 mL water:2-propanol (2:1) and transferred to tubes for size-discriminating ultrafiltration. The tubes were centrifuged for 3-4 hours at maximal speed in a standard laboratory centrifuge. The analytes were then purified on anion exchangers (Amberlyst A-26, hydroxyl ion as counter-ion or by solid phase extraction (Varian aminoprophyl bond elut) employing elution with 0.5% TFA, the eluate was evaporated and to almost dryness and the residue re-dissolved in 1 mL water:acetonitrile (1:1) and directly analyzed by LC-MS(ESI) with direct injection and/or by column separation (C$_{18}$). The solutions containing compounds 11-15 were characterized on LC-MS (ESI) in both positive and negative modes.

Synthesis of fluorescein, 5-[4-isopropyl-3-(2,3,4,5,6-pentahydroxy-hexyl)-2-thioxo-imidazolidin-5-one] (FTH-GlcVal). An aqueous solution of Val-Leu (2.0 mmol, 460 mg) and NaBH$_3$CN (3.0 mmol, 188 mg) was pH adjusted to pH 7 (using 0.1 M HCl) and thereafter reductively aminated with D-glucose (6 mmol, 1.2 g) in water (10 ml) according to Walton et al. (24). After purification on an ion-exchanger (Dowex 1×4, $^-$OAc, see ref 24) the product was dried under vacuum and, without further purification, one-third of this product was reacted with FITC (150 mg, 0.38 mmol) in 0.5 M aqueous KHCO$_3$:2-propanol (5 ml, 2:1) at 70° C. for 90 min. Aliquots of this mixture were further purified by preparative TLC (SiO$_2$, EtOAc/MeOH, 4:1) to yield compound 16. Analysis was performed as described for compounds 11-15 and LC MS analysis of this compound is presented in FIG. 16.

FITC derivatisation of reductively amimated N-terminal (1-deoxy-D-glucitol-1-yl)globin and analysis of the FTH derivatives formed. Two samples of globin (60 mg each) and one control sample (without addition of D-glucose) were incubated for three days at 45° C. with D-glucose (40 mg and 6 mg, respectively) in sodium borohydride-phosphate buffer (6 ml/sample) and 2-propanol (3 ml/sample). Subsequently, the solutions were filtrered into vivaspin tubes and the precipitated globins were reacted with FITC (20 mg, 51 pmol/sample) in aqueous pyridine (2:1) at 70° C. for 2 h. Thereafter, the samples were centrifuged in vivaspin tubes and the eluates purified on ion-exchangers utilizing elution with 0.5 M TFA. Analysis with LC-MS/MS showed that the globins incubated with D-glucose formed compound 16 (the ions formed, intensities and fragmentation patterns were identical to those of the synthetic reference compound; see FIG. 16). Compound 16 was not present at detectable levels in the control globin sample.

Simplified clean-up of samples. In order to increase the tate at which samples can be processed, a simplified clean-up procedure was developed. First blood obtained by cardiac puncture was collected in tubes (S-Monovette; Li-heparin, from Sarstedt, Sweden) and thereafter two different approaches were compared (see FIG. 19). In one case (step 1, path a;) red blood cells were isolated from 7.5-mL samples of whole blood by centrifugation at 2500 rpm for 5 minutes. Subsequently, the serum was discarded and the red blood cells were washed three times saline (7.5 ml), employing this same centrifugation. The isolated blood cells were then lysed, either by freezing (at −20° C.) or by ultrasonication (for 10 minutes). Alternatively (step 1, path b;), 7.5-mL samples of whole blood were lysed directly by freezing (at −20° C.) or ultrasonication (for 10 minutes).

Subsequent to step 1, path a, 1 mL aliquots from each sample (n=4) were transferred to the outer compartment of Centrisart I ultrafiltration tubes and diluted with 1.4 mL water. MeValLeu-NHφ (1 μg/sample; n=1), used as the internal standard, was added prior to derivatisation. FITC (8 mg/sample) was added to two of the four samples, with the remaining two serving as controls. 1 M NaOH (100 μL) and tributyl-amine (40 μL) were added to all samples with the exception of one of the controls (the pH value was 8.8 following this alkalization). After careful vortexing, all of these samples were heated for 1 h at 70° C. (step 2, path a). In the case of step 1, path b, the lysed whole blood samples (i.e., 1.5 mil/sample; n=4) were treated in exactly the same manner, except that these samples were diluted with only 0.9 mL water and heated at 38° C. for 18 h.

Following derivatization, the samples (n=8) were subjected directly to ultrafiltration with 0.6 mL ion-exchanger (Dowex 1×4, ⁻OAc) present in the inner compartment of the collection tube (see FIG. 19). Thereafter the tubes were centrifuged at 4500 rpm (for 2 h in the case of MWCO 10 000 or 4 h with MWCO 5 000) and the ion exchanger removed and washed alternately with 2 mL water and 2 mL ethanol three times. After release of the analytes from the ion exchange resin by the addition of 2% aqueous TFA (1.5 mL), this fraction can then be analyzed by injection into a LC-MS system (ESI applied) either directly and/or following injection and/or column separation ($C_{18}$), employing both the positive and negative modes. FTH-MeVal (the only adduct analysed) was detected in all samples incubated with FITC (this adduct is present as a natural occurring adduct, analysed at increased levels in the samples with internal standard added).

Results

In order to evaluate the potency of the method according to the first aspect of the present invention, the derivatives of the selected fluorescent isothiocyanate reagents (compounds 5-10, FIG. 5) were analysed and compared to the derivatives of the isothiocyanate reagents used in the N-Edman procedure (compounds 1-4, FIG. 5). Selected analytes were analysed by; $^1$H NMR (compounds 1-10), $^{13}$C NMR (1-5, 7-10), HPLC-UV (1-2, 5-6, 7-8, 9-10), LC-MS/MS (1-16), CE-DAD (9, 10) and UV/vis spectroscopy (1, 2, 6-10). Compounds 5-10 were also measured by fluorescence spectroscopy. In general, for of all these measurements and determinations, the pH was alternately below and above the pKa for the respective analyte.

NMR Results. $^1$H and $^{13}$C NMR were used in order to characterise the compounds synthesised, except for compounds 1-4, which have been synthesized and characterized earlier (Rydberg et al., 1993). Compounds 5-10 (normally 10 mg for $^1$H NMR and 40 mg for $^{13}$C NMR) were dissolved in fully deuterated solvents. The NMR analysis provides valuable information, e.g., the well separated shifts for the γ,γ'-methyls (dd, in $^1$H NMR) in the valine spin residue can be used to confirm that the compounds are fully ring-closed thiohydantoins and not precursors thereof, i.e., in the corresponding thiocarbamoylated compounds, the γ, γ'-methyls are not as well separated.

Fluorescence

The studies on the relative fluorescence of the fluorescent analytes/compound by were performed recording excitation and emission spectra, the results of which are presented in FIGS. 7-11. The FITC derivatives FTH-Val (9) and FTH-MeVal (10) exhibited the highest relative fluorescence (at pH>5) in comparison to the other reagents/compounds used. FTH-MeVal (10) was detected at a concentration 360-fold lower compared than the detectable concentration of fluoranthene (used as a reference), approximately 45-fold lower than that for DABTH-MeVal (6) and 530-fold lower than that for DNTH-MeVal (8). In addition, FTH-Val and FTH-MeVal gave almost identical results, indicating that the adduct, e.g., the methyl group in FTH-MeVal (10), does not affect its spectroscopic properties.

Liquid Chromatography

Using LC, it was possible to separate the corresponding thiohydantoins, methylated and non-methylated (i.e., 1-2, 5-6, 7-8 and 9-10), for all four reagents tested. Different gradients were used for the different reagents and, in spite of the relatively small structural differences between the methylated and the non-methylated molecules, baseline separations were achieved using a standard C-18 column. A chromatogram of the LC-MS separation is presented in FIG. 14 which documents separation of the FTH-acrylamide adduct (11), FTH-MeVal (10) and FTH-Val (9) by LC and their subsequent identification by MS. The experiment was performed using acrylamide adducts of human globin and compounds 9-11 as references (see FIG. 14).

Mass Spectrometry

In order to evaluate the suitability/applicability of the fluorescent isothiocyanate derivatives for LC-MS/MS, compounds 1-10 were compared. The cone voltage and polarity, and the pH and composition of the buffer system were varied and optimized for each analyte. The results from this study are summarized in Table 1.

TABLE 1

Comparison of relative sensitivities obtained by determinations of the limits of detection (LOD$^a$) for LC-MS/MS in the ESI and APCI modes, employing various pH modifiers/buffers.

| | Buffer: | | | | | | | | |
|---|---|---|---|---|---|---|---|---|---|
| | 0.1% NH4oAc | 0.1% TFA | 0.3 mM NH3 | Un-buffered | 0.1% TFA | NH4oAc | 0.3 mM NH3 | Un-buffered | NH4oAc |
| Ionization procedure: | ESI | ESI | ESI | ESI | APCI | ESI | ESI | ESI | APCI |
| Ions measured: | positive | Positive | positive | Positive | positive | negative | negative | negative | negative |
| FTH-MeVal | 77.0 | 18.8 | n.m$^b$ | 2180 | 1.7 | 67.1 | 1.0$^c$ | 244 | 294 |
| FTH-Val | 17.4 | 5.5 | 22.5 | 1910 | 3.1 | 7.6 | n.m | 2790 | n.m |
| DABTH-MeVal | 294 | 131 | 47.8 | 1840 | 20.4 | 220 | 272 | 1880 | n.m |
| PTH-MeVal | 48700 | 38100 | 2890 | 176600 | 3800 | 32200 | 4390 | 4360 | n.m |
| DNTH-MeVal | 4580 | 442 | 2240 | 4530 | 42.3 | 1050000 | 76600 | 4791 | n.m |

TABLE 1-continued

Comparison of relative sensitivities obtained by determinations of the limits of detection (LOD[a]) for LC-MS/MS in the ESI and APCI modes, employing various pH modifiers/buffers.

| | Buffer: | | | | | | | | |
|---|---|---|---|---|---|---|---|---|---|
| | 0.1% NH4oAc | 0.1% TFA | 0.3 mM NH3 | Un-buffered | 0.1% TFA | NH4oAc | 0.3 mM NH3 | Un-buffered | NH4oAc |
| PFPTH-HOEt | n.m | n.m | n.m | n.m | 30600 | n.m | n.m | 28500 | 1640 |
| PFPTH-MeVal | n.m | n.m | n.m | n.m | 352000 | n.m | n.m | n.m | n.m |

Footnotes;
[a]LOD were measured on positive and negative ions using direct injections and a 5 μl loop.
[b]n.m = not measured.
[c]The lowest LOD obtained (for FTH-MeVal in 0.3 mM NH3, negative ions measured; calculated to be 2.6 fmol) is set to one and the other sensitivities expressed relative to this.

Compounds 9 and 10, FTH-Val and FTH-MeVal, gave the highest response using the conditions stated for LC-MS. The LOD was 2.6 fmol ($2.6 \times 10^{-15}$ mol) for FTH-MeVal under optimal conditions, which is approximately 600-fold lower than the LOD for the traditional N-Edman reagent adduct, PTH-MeVal. This high sensitivity for the FITC derivatives is probably a result of ionizable moieties incorporated into the reagent (i.e., the carboxyl group and the phenols), which are ionized to a higher degree in the MS ion source then are the PTH and PFPTH derivatives. The results presented in Table 1 are also depicted in FIGS. 17 and 18.

In order to investigate the range of applicability for the FITC reagent, valine and globin were adducted with glycidamide and propylene oxide; reductively aminated with glucose to form a thermolabile, extremely polar adduct; and alkylated with cholesterol-5α,6α-epoxide and octadecyl-1,2-epoxide to give high-molecular weight adducts. The thiohydantoines formed (compounds 11-16) were then characterized on LC-MS/MS.

Capillary Electrophoresis

The resolution of FTH-MeVal from FTH-Val using a CE-DAD system was evaluated in order to assess the possibility of determining N-terminal adducts using separation techniques other than LC, as well as to be able to utilize and benefit from such sensitive techniques as CE-LIF. This separation was performed using the previously stated conditions i.e., 17 mM phosphate buffer (adjusted to pH 7) containing 20 mM SDS. As can be seen from FIG. 6, complete baseline separation was obtained; FTH-Val elutes after 7.44 min and FTH MeVal elutes after 8.91 min All of the fluorescent isothiocyanate reagents tested react and detach the adduct moiety with a high degree of selectivity. LC-MS/MS and LC with detection by fluorescence provide high sensitivity and selectivity and the combination of these techniques provides a powerful tool for identification of unknown compounds and for comparison of adduct patterns between and/or within species. It was observed that fluorescein isothiocyanate (FITC) was exceptional, with respect to solubility, separation and sensitivity upon analysis with MS, as well as with regards to spectroscopic properties in comparison to the other reagents tested. Thus, FITC was selected for more detailed studies using alkylated model peptides and globin. The isolated extracts were then directly and successfully analyzed by LC-MS/MS with a high degree of sensitivity and high selectivity in the system employed.

It was possible to isolate these adducts from alkylated globin derivatized with FITC by size-discriminating ultrafiltration, followed by clean-up utilizing an anion exchanger. This approach is not only time-saving, but also avoids loss of adducts, which is especially useful for analysis of adducts of high polarity, since these are often lost or recovered in poor yields in connection with liquid/liquid or solid phase extraction clean-up steps.

Simplified Preparation and Clean-up of Samples

In order to increase the rate at which samples can be processed, a simplified clean-up procedure utilizing important aspects of this invention was developed. In this context, a major goal was to minimize the number of analytical steps, required, since these steps are both time-consuming and costly. The principles of this approach are presented in FIG. 19.

In step 1, FIG. 19, blood obtained, i.e., by cardiac puncture is collected in tubes containing an anticoagulant. Subsequently, depending on the number of samples involved or the necessity for shortening the total time required for analysis, two options are available (path a or b): Path a, in which the red blood cells are isolated centrifugation and centrifugation, has the major benefit of reducing the total turnover time, especially with respect to the derivatization step (step 2 a temperature-dependent reaction), which is shortened to 1 hour and could potentially be shortened even more. In the case of path b, derivatization is performed on whole blood immediately following lysis, thereby minimizing manual handling in connection with sample preparation, an improvement which is especially valuable when handling large series of samples.

In step 2, thereafter the lysed blood cells or whole blood (step 1, path a or b, respectively) is transferred to the reaction vessels, i.e., the outer compartment of the ultracentrifugation tubes employed, containing an internal standard, preferably an N-terminal adducted peptide, e.g., MeValLeu-NHφ, in which the isothiocyanate reagent, i.e., FITC, is added. After dilution of all samples with water, the pH is elevated to approximately 9, by addition of sodium hydroxide and tertiary amines (e.g., tributyl-amine) and the samples are then heated for 1 h at 70° C. (following step 1, path a) or 18 h at 38° C. (path b). This alkalization with NaOH and tributyl-amine was found to provide several advantages, e.g., increased solubility of the FITC reagent, an increased yield of analytes and higher efficiency in connection with the ion-exchange procedure.

Subsequently, in step 3, the samples are separated from the high-molecular weight molecules hemoglobin and serum albumin utilizing size-discriminating ultracentrifugation. This procedure was further optimized by filling the inner compartment of the collection tube with an ion-exchanger (i.e., Dowex 1×4, with —OAc as the counter-ion) which binds the analytes during the period of ultracentrifugation.

With filters that retain molecules of 5 and 10 KD in molecular weight, the centrifugation times were found to be 4 and 2 hours, respectively.

If no ion-exchanger is added prior to centrifugation, the filtrate can then be analyzed directly, e.g., by CE-LIF. However, by including an ion-exchange resin compatible with the functional groups of the analytes (i.e., an anion exchanger in the case of FTH-analytes) during the centrifugation in step 3, selective and highly efficient enrichment of the sample is achieved. This procedure is illustrated in step 4 (FIG. 19). The ion-exchange resin is added directly to the inner compartment of the tube employed for size-discriminating ultrafiltration (step 3) and washed with water and ethanol in order to remove impurities of low-to-medium molecular weight.

Following ultracentrifugation, the analytes are released from the ion-exchange resin by the addition of acid, i.e., 2% aqueous TFA. This procedure can be further improved by placing the ion-exchanger in a cylindrical container which fits snugly into the inner compartment of the tube, providing direct contact with the eluate. In this manner the container can easily be removed, washed with suitable solvents and acidified or alkalized (depending on the choice of ion-exchanger) in order to release the analytes. The filtrate can then be analyzed directly (step 3, path b in FIG. 19) by, e.g., CE-LIF, LC-MS/MS, etc., or preferably after performance of step 4, path a by, e.g., LC-MS/MS, or following alkalization of the detached analytes by, e.g., CE-LIF.

In summary, depending on which of the paths described above is chosen for the clean-up procedure, the time required for analysis varies from 3.5 h to 20 h. This choice of path is determined by the number of samples to be analysed and the separation and detection techniques to be employed. The most rapid through-put of samples, is obtained by utilizing step 1, path b, which minimizes the amount of the laboratory work required to process each sample.

In comparison to the traditional N-alkyl Edman procedure the invented method described above, reduces the number of individual steps in the analytical chain from seven (i.e., sampling; isolation and washing of red blood cells; isolation of globin by acid precipitation; drying of globin; derivatization of globin with PFPITC; extraction of the reaction mixture; and concentration of the analytes by evaporation prior to measurement by GC-MS/MS; see references 7 and 18) to 3 or 4 steps. Altogether, the N-alkyl Edman procedure takes about 2 days to complete analysis of a limited number of samples; whereas the fluorescenvionizable N-R-Edman procedure described here minimizes time to 3.5-20 h while providing excellent sensitivity. This opens up the possibility for large-scale analysis, screening of large sets of samples manually or by automation of the analytical procedure described above.

The results presented above also show that the FITC derivatives FTH-Val (9) and FTH-MeVal (10) can be efficiently separated by CE (FIG. 6) and monitored using fluorescence detection at specific excitation and emission at wavelengths (approximately 492 and 515 nm, respectively) (FIG. 15). Consequently, these FITC derivatives can be excited using an Argon-ion laser (488 nm), opening up the possibility of employing CE-LIF for measurement of zmol ($10^{-21}$) levels of adducts. These results are truly encouraging for miniaturization of the fluorescent-N-R Edman procedure, with the aim of characterizing adducts in a few µL blood, easily available by a prick on the fingertip, thereby enabling routine analyses on a much larger scale. Furthermore, as-yet-unknown adducts may detected and be analyzable in the future as a result of this high sensitivity.

Various embodiments of the present invention have been described above, but a person skilled in the art envisions further minor alterations, which would fall into the scope of the present invention. The breadth and scope of the present invention should not be limited by any of the examples of embodiment described above, but should be defined only in accordance with the following claims and their equivalents. For example, any of the methods noted above can be combined with other known methods. Other aspects, advantages and modifications within the scope of the invention will be apparent to those skilled in the art to which this invention pertains.

REFERENCES

1. Ehrenberg, L., Hiesche, K. D., Osterman-Golkar, S. and Wennberg, I. (1974) Evaluation of genetic risks of alkylating agents: Tissue doses in the mouse from air contaminated with ethylene oxide. *Mutat. Res.* 24, 83-103.
2. Osterman-Golkar, S., Ehrenberg, L., Segerback, D. and Hallstrom, I. (1976) Evaluation of genetic risks of alkylating agents. II. Haemoglobin as a dose monitor. *Mutat. Res.* 34, 1-10.
3. Neumann, H. G., Baur. H and Wirsing. R. (1980) Dose-response relationship in the primary lesion of strong electrophilic carcinogens. *Arch. Toxicol. Suppl.* 3, 69-77.
4. Skipper, P. L. and Tannenbaum, S. R. (1990) Protein adducts in the molecular dosimetry of chemical carcinogens. *Carcinogenesis* 11, 507-518.
5. Törnqvist, M., Fred, C., Haglund, J., Helleberg, H., Paulsson, B. and Rydberg, P. (2002) Protein adducts: quantitative and qualitative aspects of their formation, analysis and applications. *J. Chromatogr.* B 778, 279-308.
6. Osterman-Golkar S. and Ehrenberg, L. (1980) Alkylation of macromolecules for detecting mutagenic agents. *Teratog. Carcinog. Mutag.* 1, 105-127.
7. Jensen, S., Törnqvist, M. and Ehrenberg, L. (1984) Hemoglobin as a dose monitor of alkylating agents: Determination of alkylation products of N-terminal valine. (F. J. de Serres and R. W. Pero, Ed.) pp 315-320, Plenum Press, New York
8. Edman, P. (1950) Methods for determination of the amino acid sequence in peptides. *Acta Chem. Scand.* 4, 283-298.
9. Edman, P. and Henschen, A. (1975) Sequence determination. In *Protein Sequence Determination* (Needleman S. B., Ed.) pp 232-279, Springer-Verlag, Berlin
10. Törnqvist, M., Mowrer, J., Jensen, S. and Ehrenberg, L. (1986) Monitoring of environmental cancer initiators through hemoglobin adducts by a modified Edman method. *Anal. Biochem.* 154, 255-266.
11. Tates, A. D., Grummt, T., Törnqvist, M., Farmer, P. B., van Dam, F. J., van Mossel, H., Schoemaker, H. M., Osterman-Golkar, S., Uebel, C., Tang, Y. S., Zwinderman, A. H., Natarajan, A. T. and Ehrenberg, L. (1991) Biological and chemical monitoring of occupational exposure to ethylene oxide. *Mutat. Res.* 250, 483-497.
12. Törnqvist, M., Magnusson, A. L., Farmer, P. B., Tang, Y. S., Jeffery, A. M., Wazneh, L., Beulink, G. D. T., van derWaal, H. and van Sittert, N. J. (1992) Ring test for low-levels of N-(2-hydroxyethyl)valine in human hemoglobin. *Anal. Biochem.* 203, 357-360.
13. Bergmark, E., Calleman, C. J., He, F. and Costa, L. G. (1993) Hemoglobin adducts in humans occupationally exposed to acrylamide. *Toxicol. Appl. Pharmacol.* 120, 45-54.
14. Fidder, A., Noort, D., de Jong, A. L., Trap, H. C., de Jong, L. P. and Benschop, H. P. (1996) Monitoring of in vitro and in vivo exposure to sulfur mustard by GC/MS determination of the N-terminal valine adduct in Hb after a modified Edman degradation. *Chem. Res. Toxicol.* 9, 788-792.
15. Thier, R., Lewalter, J., Kempkes, M., Selinski, S., Bruning, T. and Bolt, H. M. (1999) Haemoglobin adducts of acrylonitrile and ethylene oxide in acrylonitrile workers, dependent of polymorphisms of the glutathione transferases GSTT1 and GSTM1. *Occup. Environ. Med.* 56, 197-202.
16. Begemann, P., Sram, R. J. and Neumann, H. G. (2001) Hemoglobin adducts of epoxybutene in workers occupationally exposed to 1,3-butadiene. *Arch. Toxicol.* 74, 680-687.
17. Törnqvist, M. (1994) Epoxide adducts to N-terminal valine of hemoglobin. In *Methods Enzymol.* (Everse J., Vandergriff K. D. and Winslow R. W., Eds.) pp 650-657, Academic Press, New York
18. Paulsson, B., Athanassiadis, I., Rydberg, P. and Törnqvist, M. (2003) Hemoglobin adducts from glycidamide: acetonization of hydrophilic groups for reproducible gas chromatography/tandem mass spectrometric analysis. *Rapid Commun. Mass. Spectrom.* 17, 1859-1865.
19. Ireland, I. D., Lewis, D. F., Li, X., Renborg, A., Kwong, S., Chen, M. and Dovichi, N. J. (1997) Duoble Coupling Edman Chemistry for High-sensitivity Automated Protein Sequencing. *J. Protein Chem.* 16, 491-493.
20. Ospina, M., Vesper, H., Licea-Perez. H. and Luchuan, G. L. LC/MS/MS method for the analysis of acrylamide and glycidamide hemoglobin adducts. 227$^{th}$ ACS national meeting, Anaheim, Calif., 29-31, Mar. 2004.
21. Rydberg, P., Luning, B., Wachtmeister, C. A. and Törnqvist, M. (1993) Synthesis and characterization of N-substituted valines and their phenyl-thiohydantoins and pentafluorophenyl-thiohydantoins. *Acta Chem. Scand.* 47, 813-817.
22. Payne, G. B. and Williams, P. H. (2004) Reaction of hydrogen peroxide. VI. Alkaline epoxidation of acrylonitrile. *JOC.* 26, 651-659.
23. Mowrer, J., Törnqvist, T., Jensen, S. and Ehrenberg, L. (1986) Modified Edman degradation applied to haemoglobin for monitoring occupational exposure to alkylating agents. *Toxicol. Environ. Chem.* 11, 215-231.
24. Walton, D. J., Ison, E. R. and Szarek, W. A. (1984) Synthesis of N-(1-deoxyhexitol-1-yl)amino acids, reference compounds for the nonenzymatic glycosylation of proteins. Carbonhydrate Res. 128, 37-49.

The invention claimed is:

1. Method for analyzing adducts in a fluid and/or solid material suspected of containing said adducts, wherein said adduct is an N-adducted amino acid or adducted N-terminal peptide/protein, comprising the following steps:
   a) bringing said fluid and/or solid material in direct contact with an isothiocyanate reagent wherein said reagent is an isothiocyanate reagent containing a fluorescent moiety and an ionizable moiety selected from the group consisting of FITC, DNITC and DABITC or a derivative thereof;
   b) allowing said reagent to react with adducted N-terminals in proteins or peptides present in said fluid and/or solid material;
   c) separating the analytes formed from the reaction mixture; and
   d) detecting the analytes formed, and optionally visualizing the result, wherein step c) is performed using LC and step d) is performed using MS detection.

2. A method according to claim 1 wherein the detection step d) is followed by a step e) comparing the results from the detection step d) with previously obtained results, obtained using steps a)-d), which previously obtained results emanate from a standard material formed from the adduct under scrutiny, and optionally calculating a quotient between said results and optionally presenting said quotient visually.

3. A method according to claim 1 wherein said adducted N-terminals have their adducts attached to a secondary N-terminal valine in hemoglobin, a secondary N-terminal asparagine in serum albumin or to a secondary N-terminal glycine in myoglobin.

4. A method according to claim 1 wherein said adduct is a globin adduct.

5. A method according to claim 1 wherein said adduct is a hemoglobin or a myoglobin adduct.

6. A method according to claim 1 wherein said adduct is a serum albumin adduct.

7. A method according to claim 1 wherein said reagent is FITC.

8. A method according to claim 1 wherein step c) is preceded by a step for enriching the analyte present.

9. A method according to claim 8 wherein said enrichment step preceding step c) is performed using size-discriminating ultrafiltration, or ultracentrifugation.

10. A method according to claim 1 wherein said analyte is a compound according to formula I or II, or a derivative thereof:

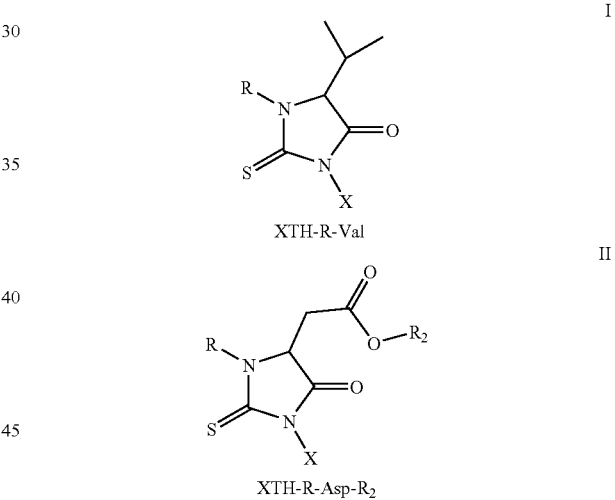

wherein R represents any adduct (e.g., alkyl and aryl or substituted analogues thereof, with the exception for hydrogen) and X represents a moiety of any isothiocyanate reagent utilized in which the isothiocyanate group is directly bound to an aromatic ring or an aromatic ring system providing fluorescent and/or ionizable properties to the analyte, with the exception that X is not a phenyl, 4-bromophenyl, 4-methoxyphenyl or pentafluorophenyl group, and $R_2$ represents hydrogen, an alkyl, aryl, carboxyl or benzyl group or substituted analogues thereof; or a carboxyl anion group.

11. A method according to claim 1 wherein detection of the analyte in step d) is performed at a pH above 5.

12. A method according to claim 1 wherein said fluid and/or solid material is blood or processed blood, which has been obtained at an earlier stage.

13. A method according to claim 12 wherein the blood is processed either by centrifugation, washing and lysating, or lysating only.

14. A method according to claim 13 wherein said centrifugation, washing and lysating is followed by heating at approximately 70° C.

15. A method according to claim 13 wherein said lysating only, is followed by heating at approximately 38° C.

16. A method according to claim 14 wherein the heating is followed by step c) as set out in claim 1 wherein the separation is performed by size discriminating ultra filtration in a size-discriminating ultra filtration tube and whereupon the analyte is being bound to an ion exchange resin in said tube and thereupon purifying said analyte.

17. A method according to claim 16 wherein the purifying of said analyte is performed by first washing the resin to which the analyte is bound and release the analyte from the resin preferably by adding an acid to said resin, and subsequently filter the resin off giving the analyte in the remaining filtrate.

18. A method according to claim 17 wherein the detecting as set out in step d) of claim 1 is performed by using LC-MS/MS.

19. A method according to claim 18 wherein alkalization of the detached analytes is performed before detecting using CE-LIF.

20. A method according to claim 15 wherein the heating is followed by step c) as set out in claim 1 wherein the separation is performed by size-discriminating ultra filtration in a size-discriminating ultra filtration tube and wherein the analyte is free in solution and present in the filtrate.

21. A method according to claim 20 wherein the detecting as set out in step d) of claim 1 is performed by using LC-MS/MS.

22. A method for manufacturing a standard material for use in a method according to claim 1 comprising the following steps:
   i) reacting an N-substituted amino acid or an adducted N-terminal in a protein or a peptide with a reagent wherein said reagent is an isothiocyanate reagent containing a fluorescent and an ionizable moiety selected from the group consisting of FITC, DNITC and DABITC or a derivative thereof; and
   ii) purifying the analyte, which is a thiohydantoin analyte formed, by, e.g., separating the unreacted compound from the reaction mixture.

23. A method according to claim 22 wherein said adducted N-terminals have their adducts attached to a secondary N-terminal valine in hemoglobin, a secondary N-terminal asparagine in serum albumin or a secondary N-terminal glycine in myoglobin.

24. A method according to claim 22 wherein said adduct is a globin adduct.

25. A method according to claim 24 wherein said adduct is a hemoglobin or a myoglobin adduct.

26. A method according to claim 22 wherein said adduct is a serum albumin adduct.

27. A method according to claim 22 wherein said reagent is FITC.

28. A method according to claim 22 wherein said analyte is a compound according to formula I or II or a derivative thereof;

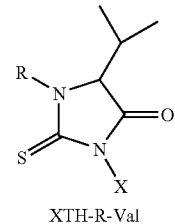

XTH-R-Val

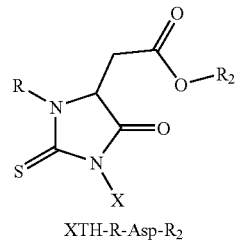

XTH-R-Asp-R$_2$ wherein R represents any adduct (e.g., alkyl and aryl or substituted analogues thereof, with the exception of hydrogen) and X represents a moiety of any isothiocyanate reagent utilized in with the isothiocyanate group is directly bound to an aromatic ring or an aromatic ring system, thereby providing fluorescent and/or ionizable properties to the analyte, which the exception that X is not a phenyl, 4-bromophenyl, 4-methoxyphenyl or pentafluorophenyl group, and R$_2$ represents hydrogen; an alkyl, aryl, carboxyl or benzyl moiety or substituted analogues thereof; or a carboxyl anion group.

29. A method according to claim 22 wherein said analyte is a compound selected from the group consisting of 3-[4-(4-dimethylamino-phenylazo)-phenyl]-5-isopropyl-1-methyl-2-thioxo-imidazolidin-4-one (DABTH-MeVal); 3-(4-dimethylamino-naphthalen-1-yl)-5-isopropyl-1-methyl-2-thioxo-imidazolidin-4-one (DNTH-MeVal); fluorescein, 5-(4-isopropyl-3-methyl-2-thioxo-imidazolidin-5-one) (FTH-MeVal); fluorescein, 5-[4 isopropyl-3-(2-carbamoyl-ethyl)-2-thioxo-imidazolidin-5-one] (FTH-AAVal); fluorescein, 5-[4-isopropyl-3-(2-carbamoyl-2-hydroxy-ethyl)-2-thioxo-imidazolidin-5-one] (FTH-GAVal); fluorescein, 5-[4-isopropyl-3-(2-hydroxyoctadecyl)-2-thioxo-imidazolidin-5-one] (FTH-HOC$_{18}$Val); fluorescein, 5-[4-isopropyl-3-(2-hydroxy-propyl)-2-thioxo-imidazolidin-5-one] (FTH-HOPrVal); fluorescein, 5-{4-isopropyl-3-[17-(1,5-dimethylhexyl)-3,5 and/or 6-dihydroxy-10,13-dimethyl-hexadecahydro-cyclopenta[a]phenanthren-5 and/or 6-yl])-2-thioxo-imidazolidin-5-one} (FTH-CholEOVal) and fluorescein, 5-[4-isopropyl-3-(2,3,4,5,6-pentahydroxy-hexyl)-2-thioxo-imidazolidin-5-one] (FTH-GlcVal).

30. A standard material obtainable by the method according to claim 22.

31. A compound selected from the group consisting of 3-[4-(4-dimethylamino-phenylazo)-phenyl]-5-isopropyl-1-methyl-2-thioxo-imidazolidin-4-one (DABTH-MeVal); 3-(4-dimethylamino-naphthalen-1-yl)-5-isopropyl-1-methyl-2-thioxo-imidazolidin-4-one (DNTH-MeVal); fluorescein, 5-(4-isopropyl-3-methyl-2-thioxo-imidazolidin-5-one) (FTH-MeVal); fluorescein, 5-[4-isopropyl-3-(2-carbamoyl-ethyl)-2-thioxo-imidazolidin-5-one] (FTH-AAVal); fluorescein, 5-[4-isopropyl-3-(2-carbamoyl-2-hydroxy-ethyl)-2-thioxo-imidazolidin-5-one] (FTH-GAVal); fluorescein, 5-[4-isopropyl-3-(2-hydroxyoctadecyl)-2-thioxo-imidazolidin-5-one] (FTH-HOC$_{18}$Val); fluorescein, 5-[4-isopropyl-3-(2- hydroxypropyl)-2-thioxo-imidazolidin-5-one] (FTH-HOPrVal); fluorescein, 5-{4-isopropyl-3-[17(1,5-dimethyl-hexyl)-3,5 and/or 6-dihydroxy-10,13-dimethyl-hexadecahydro cyclopenta[a]phenanthren-5 and/or 6-yl])-2-thioxo-imidazolidin-5-one} (FTH-CholEOVal) and fluorescein, 5-[4-isopropyl-3-(2,3,4,5,6-pentahydroxy-hexyl)-2-thioxo-imidazolidin-5-one] (FTH-GlcVal).

32. A container for use when analyzing adducts in a fluid or a solid material suspected of containing said adducts, wherein said container provides means for performing steps a) c) as set out in claim 1.

33. A kit containing standard material according to claim 30.

34. A kit containing a compound according to claim 31 and a container.

35. An apparatus for performing the method according to claim 1 and providing means for performing steps a)-c) and for the detection in step d).

36. A computer program stored on a data carrier for performing the method according to claim 1.

37. A method according to claim 9, wherein said size-discriminating ultrafiltration is followed by an ion-exchanging step.

38. A method according to claim 9, wherein said ultracentrifugation is followed by an ion-exchanging step.

39. A method according to claim 1, wherein the detection of the analyte in step d) is performed at a pH of approximately 7.

40. A method according to claim 12 wherein said fluid and/or solid material is blood or processed blood of human origin.

41. A method according to claim 12 wherein said fluid and/or solid material is blood or processed blood which has been obtained at an earlier stage contained in a container.

42. A method according to claim 41 wherein said fluid and/or solid material is blood or processed blood which has been obtained at an earlier stage contained in a tube.

43. A method according to claim 14 wherein said centrifugation, washing and lysating is followed by heating at approximately 70° C. for approximately 1 hour.

44. A method according to claim 15 wherein said lysating only, is followed by heating at approximately 38° C. for approximately 18 hours.

45. A method according to claim 17 wherein the purifying of said analyte is performed by first washing the resin to which the analyte is bound and release the analyte from the resin by adding an acid to said resin, and subsequently filter the resin off giving the analyte in the remaining filtrate.

* * * * *